(12) United States Patent
Ogasawara et al.

(10) Patent No.: US 9,458,515 B2
(45) Date of Patent: Oct. 4, 2016

(54) RNA INCLUDING NUCLEOSIDE COMPOUND, METHOD FOR REGULATING AMOUNT OF PROTEIN PRODUCED FROM THE RNA, AND NUCLEOSIDE COMPOUND

(75) Inventors: Shinji Ogasawara, Wako (JP); Mizuo Maeda, Wako (JP)

(73) Assignee: RIKEN, Wako-shi, Saitama (JP)

( * ) Notice: Subject to any disclaimer, the term of this patent is extended or adjusted under 35 U.S.C. 154(b) by 353 days.

(21) Appl. No.: 13/582,674

(22) PCT Filed: Feb. 18, 2011

(86) PCT No.: PCT/JP2011/053577
§ 371 (c)(1),
(2), (4) Date: Nov. 7, 2012

(87) PCT Pub. No.: WO2011/111501
PCT Pub. Date: Sep. 15, 2011

(65) Prior Publication Data
US 2013/0052710 A1 Feb. 28, 2013

(30) Foreign Application Priority Data
Mar. 11, 2010 (JP) .................. 2010-055135

(51) Int. Cl.
C12N 15/11 (2006.01)
C12Q 1/68 (2006.01)
C07H 19/20 (2006.01)
C07H 19/167 (2006.01)
C07H 19/173 (2006.01)
C07H 21/02 (2006.01)

(52) U.S. Cl.
CPC ........... *C12Q 1/6897* (2013.01); *C07H 19/167* (2013.01); *C07H 19/173* (2013.01); *C07H 19/20* (2013.01); *C07H 21/02* (2013.01)

(58) Field of Classification Search
USPC .................. 435/173.1; 536/23.1, 27.21, 27.6, 536/27.81, 28.4, 28.5, 28.53
See application file for complete search history.

(56) References Cited

U.S. PATENT DOCUMENTS 6,812,209 B1 11/2004 Sinn et al.
2001/0012885 A1 8/2001 Sinn et al.

FOREIGN PATENT DOCUMENTS

| JP | 2009-114171 A | 5/2009 |
| JP | 2010-241754 A | 10/2010 |
| WO | 96/09071 | 3/1996 |
| WO | 2004/046321 | 6/2004 |

OTHER PUBLICATIONS

Liu et al.; Azobenzene-tethered T7 promoter for efficient photoregulation of transcription; Journal of the American Chemical Society; vol. 128, pp. 1009-1015, available online Dec. 24, 2005.*

Asanuma et al.; Synthesis of azobenzene-tethered DNA for reversible photo-regulation of DNA functions: hybridization and transcription; Nature Protocols; vol. 2, No. 1, pp. 203-212, available online Feb. 8, 2007.*
Kamiya et al.; Synthetic Gene Involving Azobenzene-Tethered T7 Promoter for the Photocontrol of Gene Expression by Visible Light; ACS Synthetic Biology, pp. A-F, available online Aug. 21, 2014.*
Ogasawara et al.; Photoresponsive 5′-cap for the reversible photoregulation of gene expression; Bioorganic & Medicinal Chemistry Letters; vol. 21, pp. 5457-5459; available online Jul. 7, 2011.*
Ogasawara, Shinji, et al. "Development of Biocompatible Photochromic Nucleobase", CSJ: The Chemical Society of Japan, Mar. 12, 2010, vol. 90th, No. 3, p. 760, 4D3-04.
Ando, H. et al., "Photo-mediated gene activation using caged RNA/DNA in zebrafish embryos", Nat. genetics. Aug. 2001, vol. 28, p. 317-325.
Ogasawara, S. et al., "Synthesis and reversible photoisomerization of photoswitchable nucleoside, 8-styryl-2′-deoxyguanosine", Tetrahedron Lett. 2008, 49, p. 2479-2482.
Miyaura, N. et al., "Palladium-Catalyzed Cross-Coupling Reaction of Organoboron Compounds", Chem. Rev., 1995, 95, p. 2457-2483.
Amann, N. et al., "Preparation of Pyrenyl-Modified Nucleosides via Suzuki-Miyaura Cross-Coupling Reactions", Synlett, 2002, No. 5, p. 687-691.
Yoshikawa, Isao et al., "Nucleoside-based organogelators: gelation by the G-G base pair formation of alkylsilylated guanosine derivatives", Tetrahedron 63, 2007, p. 7474-7481.
Davis, Jeffery T. et al., "Supramolecular architectures generated by self-assembly of guanosine derivatives", The Royal Society of Chemistry, Chem. Soc. Rev., 2007, 36, p. 296-313.
Spada, Gian Piero et al., "The Disclosure of the Stepwise Supramolecular Organization of Guanosine Derivatives: Serendipity or Programmed Design?", Synlett, 2004, No. 4, p. 596-602.
Ogasawara, S. et al., "Photo-controllable aptamer", Nucleic Acids Symposium Series, 2009, vol. 53, No. 1, p. 195-196.
Ogasawara, S. et al., "Reversible Photoswitching of a G-Quadruplex", Angew. Chem. Int. Ed., 2009, vol. 48, p. 6671-6674.
Ogasawara, S. et al., "Photochromic Nucleobase: Reversible Photoisomerization, Photochemical Properties and Photoregulation of hybridization", Nucleic Acids Symposium Series, 2008, vol. 52, No. 1, p. 369-370.

(Continued)

*Primary Examiner* — Antonio Galisteo Gonzalez
(74) *Attorney, Agent, or Firm* — Casmir Jones, SC

(57) ABSTRACT

An RNA of the present invention is an RNA containing a 5′ cap structure and a coding region having a 5′ initiation codon and a 3′ stop codon on both ends of the coding region, the RNA having a nucleoside compound introduced at a site selected from among the 5′ cap structure and 10 bases from a 5′ end of the RNA, wherein the nucleoside compound is such that a group is attached to (i) a carbon atom at position 8 of a purine nucleus or (ii) a carbon atom at position 5 or 6 of a pyrimidine nucleus, the group being represented by formula (I):

$$A-X=X-\# \quad \text{(I)}$$

where A represents an aryl group or a heteroaryl group, # represents a site where the group represented by the formula (I) is attached to the carbon atom at the position 8 of the purine nucleus or the carbon atom at the position 5 or 6 of the pyrimidine nucleus, and two Xs, which are identical to or different from each other, each represents a nitrogen atom or CH whose H may be substituted by alkyl.

8 Claims, 6 Drawing Sheets

(56) References Cited

OTHER PUBLICATIONS

Ogasawara, S. et al., "Straightforward and Reversible Photoregulation of Hybridization by Using a Photochromic Nucleoside", Angew. Chem. Int. Ed. 2008, vol. 47, p. 8839-8842.

Saito, Y. et al., "Fluorescence switching of photochromic vinylpyrene-substituted 2'-deoxyguanosine", Tetrahedron Letters, 2009, vol. 50, No. 13, p. 1403-1406.

Lawson, T. et al., "Different Patterns of Mutagenicity of Arenediazonium Ions in V79 Cells and *Salmonella typhimurium* TA102: Evidence for Different Mechanisms of Action", Journal of Agricultural and Food Chemistry, 1995, vol. 43, No. 10, p. 2627-35.

Lee, C.-Y. et al., "Characteristics of 8-Substituted Adenine Nucleotide Derivatives Utilized in Affinity Chromatography", Archives of Biochemistry and Biophysics, 1975 vol. 168, No. 2, p. 665-676.

Ikeda, K. et al., "Conversion of Uridine into Isouramil Nucleosides and Related Reactions", Pharmaceutical Society of Japan, Chemical & Pharmaceutical Bulletin, 1973, vol. 21, No. 6, p. 1327-1332.

Ikeda, K. et al., "Reactions of Uracil Derivatives with Phenylhydrazine", Pharmaceutical Society of Japan, Chemical & Pharmaceutical Bulletin, 1971, vol. 19, No. 3, p. 564-570.

English translation of International Search Report, PCT/JP2011/053577, dated Mar. 22, 2011.

* cited by examiner

F I G. 6
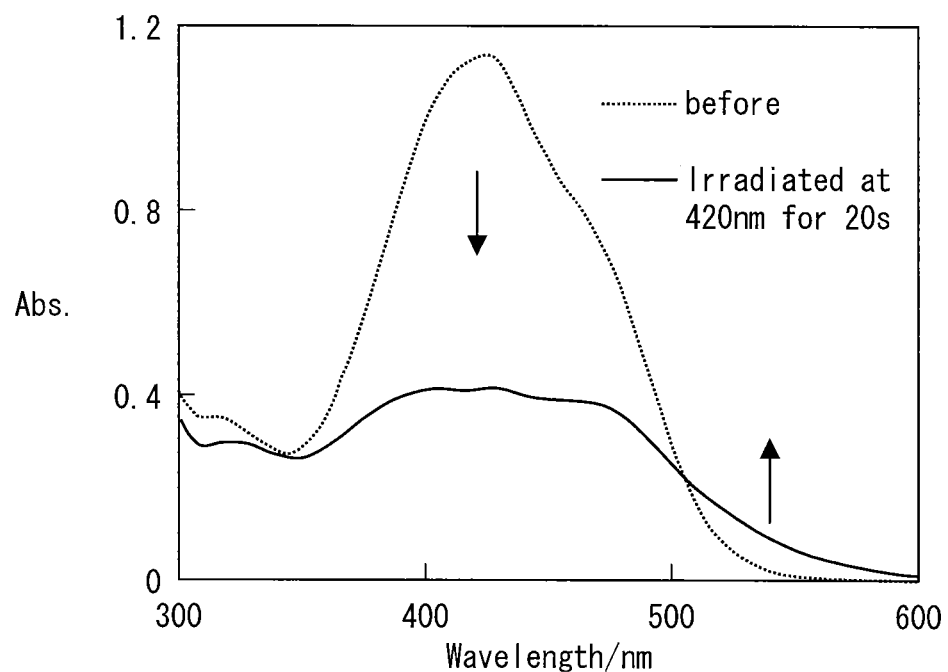
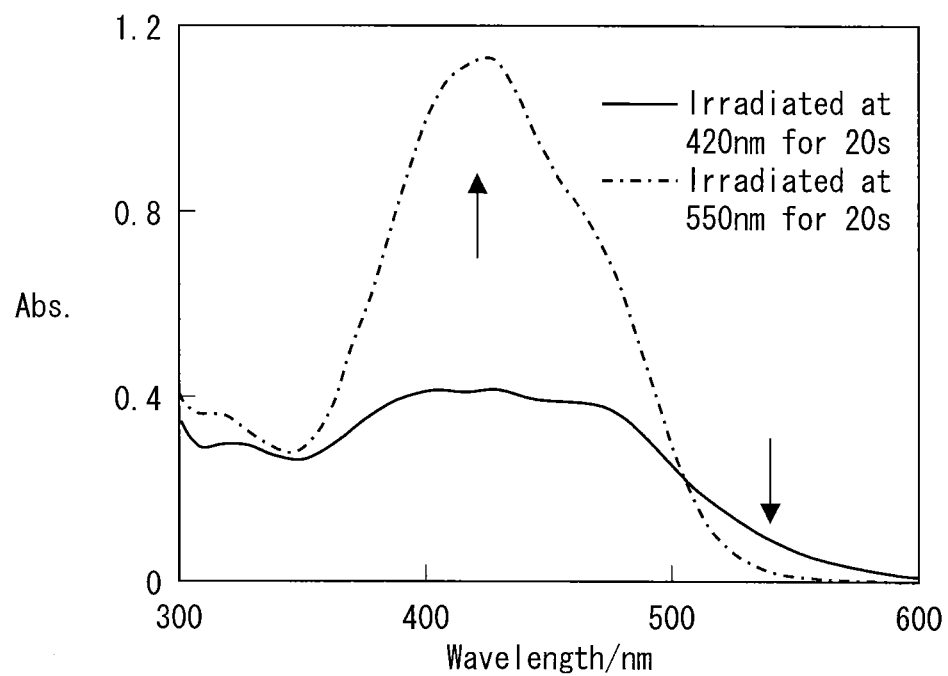

RNA INCLUDING NUCLEOSIDE COMPOUND, METHOD FOR REGULATING AMOUNT OF PROTEIN PRODUCED FROM THE RNA, AND NUCLEOSIDE COMPOUND

CROSS-REFERENCE TO RELATED APPLICATIONS

This application is a national stage of International (PCT) Patent Application Serial No. PCT/JP2011/053577, filed Feb. 18, 2011, which claims the benefit of and priority to JP Patent Application No. 2010-055135 filed Mar. 11, 2010, the contents of each of which are hereby incorporated by reference for all purposes.

TECHNICAL FIELD

The present invention relates to an RNA containing a nucleoside compound, a method for regulating the amount of protein produced from the RNA, and a nucleoside compound. The RNA is such that translation of the RNA can be regulated by photoisomerization of the nucleoside compound.

BACKGROUND ART

To strictly regulate the protein expression in a short period, it is necessary to regulate a process of protein translation from mRNA. This is because in case transcription from DNA to mRNA is regulated by inhibiting the transcription, the translation will not stop until mRNA is degraded.

There is a technique of stopping the translation of mRNA introduced into a cell, until the mRNA is irradiated with light having a predetermined wavelength (Non-Patent Literature 1). In this technique, a caged compound is bound in advance to mRNA to be injected, so that the caged compound prevents ribosome from moving on the mRNA. The caged compound is dissociated from the mRNA upon receipt of light having a predetermined wavelength. By utilizing this technique, it therefore is possible to initiate the translation of mRNA at a desired timing.

CITATION LIST

Patent Literature

Patent Literature 1
Japanese Patent Application Publication, Tokukai, No. 2009-114171 A (Publication Date: May 28, 2009)

Non-Patent Literatures

Non-Patent Literature 1
H. Ando, T. Furuta, R. Y. Tsien, H. Okamoto "Photo-mediated gene activation using caged RNA/DNA in zebrafish embryos" Nat. genetics. 2001, 28, 317-325.
Non-Patent Literature 2
S. Ogasawara, I. Saito, M. Maeda "Synthesis and reversible photoisomerization of photoswitchable nucleoside, 8-styryl-2'-deoxyguanosine" Tetrahedron Lett. 2008, 49, 2479-2482.
Non-Patent Literature 3
S. Ogasawara, M. Maeda "Straightforward and Reversible Photoregulation of Hybridization using Photochromic Nucleoside" Angew. Chem. Int. Ed. 2008, 47, 8839-8842.
Non-Patent Literature 4
S. Ogasawara, M. Maeda "Reversible Photoswitching of a G-Quadruplex" Angew. Chem. Int. Ed. 2009, 48, 6671-6674.

SUMMARY OF INVENTION

Technical Problem

However, in the above-described conventional technique, once the translation is initiated, the translation does not stop until the mRNA is degraded. This is because the dissociated caged compound does not bind to the mRNA. Thus, it is not possible to regulate the amount of produced protein. Furthermore, after the irradiation with light for dissociating the caged compound from the mRNA, the mRNA spreads beyond an area irradiated with light. Protein translation of the mRNA thus spread beyond the area does not stop, and it therefore is impossible to locally express a desired protein. That is, it is impossible to reversibly switchably regulate local protein expression in a cell by the conventional technique.

It is known that an undifferentiated cell, for example, has a specific region in which a specific mRNA is localized, and protein translation can be carried out in the region in a specific period. Temporary expression of a protein in such a specific region can determine what type of cell to be differentiated. That is, for the development of a regenerative medical technique and the like techniques that require precise regulation of the biological phenomena or for the study aimed to elucidate further biological phenomena, there is an increasing demand for a technique of regulating the amount of produced protein by causing protein translation of a specific mRNA in a specific region at a desired timing over a specific period of time and stopping the translation after a lapse of the specific period of time.

In view of the above-described background, an object of the present invention is to provide an RNA from which the amount of protein produced can be regulated as desired by irradiation with light having a specific wavelength.

Solution to Problem

In order to solve the above problem, an RNA of the present invention is an RNA containing a 5' cap structure and a coding region having a 5' initiation codon and a 3' stop codon on both ends of the coding region, the RNA having a nucleoside compound introduced at a site selected from among the 5' cap structure and 10 bases from a 5' end of the RNA, wherein the nucleoside compound is such that a group is attached to (i) a carbon atom at position 8 of a purine nucleus or (ii) a carbon atom at position 5 or 6 of a pyrimidine nucleus, the group being represented by formula (I):

[Chem. 1]

$$A\text{-}X\text{=}X\text{-}\# \qquad (I)$$

where A represents an aryl group or a heteroaryl group, # represents a site where the group represented by the formula (I) is attached to the carbon atom at the position 8 of the purine nucleus or the carbon atom at the position 5 or 6 of the pyrimidine nucleus, and two Xs, which are identical to or different from each other, each represents a nitrogen atom or CH whose H may be substituted by alkyl.

Further, in order to solve the above problem, a method for regulating the amount of protein produced from the RNA of the present invention, includes the step of: irradiating the RNA with first light and/or with second light, the first light having a wavelength to change a structure of a nucleoside compound from a trans form to a cis form by irradiation of the first light, the second light having a wavelength to change the structure of the nucleoside compound from the cis form to the trans form by irradiation of the second light.

Still further, a nucleoside compound of the present invention is such that a group is attached to (i) a carbon atom at position 8 of a purine nucleus or (ii) a carbon atom at position 5 or 6 of a pyrimidine nucleus, the group being represented by formula (I'):

[Chem. 2]

A-X=X-# (I')

where A represents an aryl group or a heteroaryl group, # represents a site where the group represented by the formula (I') is attached to the carbon atom at the position 8 of the purine nucleus or the carbon atom at the position 5 or 6 of the pyrimidine nucleus, and two Xs are identical and represent nitrogen atoms.

Advantageous Effects of Invention

The present invention yields the effect of providing an RNA with which the amount of protein produced by translation of the RNA can be regulated in a reversible switchable fashion at a selected place and in a selected period.

BRIEF DESCRIPTION OF DRAWINGS

FIG. 6 is a view showing changes in absorption spectra of a compound obtained in Example 4 when irradiated with light at 420 nm (in a upper part) and light at 550 nm (in a lower part).

DESCRIPTION OF EMBODIMENTS

Figure 1:
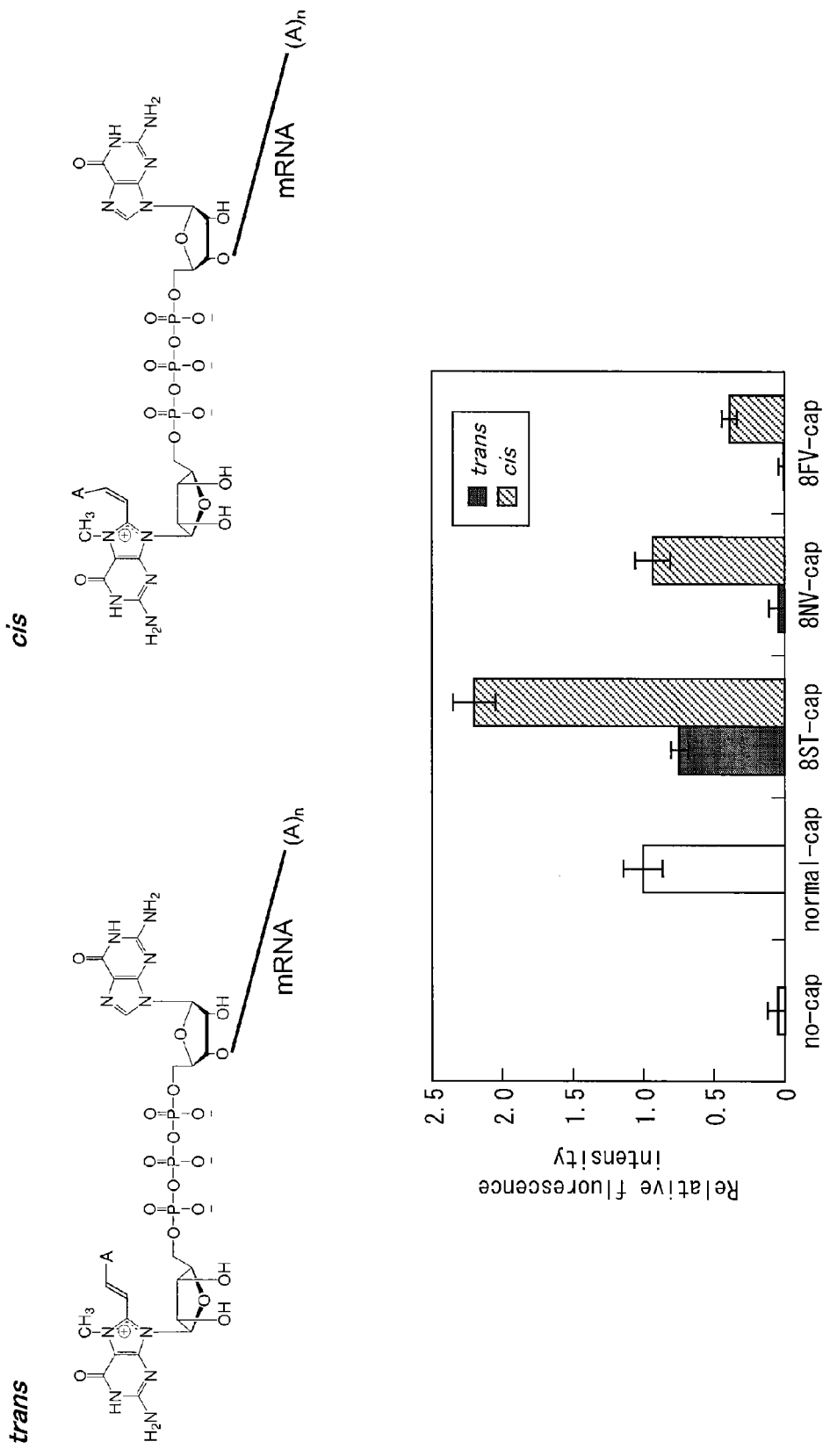
FIG. 1 is a view showing a schematic structure of an RNA as used in Example 1 and showing the comparison in translation level of the RNA and translational photoregulation.

[RNA According to the Present Invention]
(Structure of the RNA)

An RNA according to the present invention contains a 5' cap structure and a coding region having a 5' initiation codon and a 3' stop codon on both ends of the coding region. The RNA according to the present invention has a nucleoside compound introduced at a site selected from among the 5' cap structure and 10 bases from a 5' end of the RNA, wherein the nucleoside compound is such that a group is attached to (i) a carbon atom at position 8 of a purine nucleus or (ii) a carbon atom at position 5 or 6 of a pyrimidine nucleus, the group being represented by formula (I):

[Chem. 3]

A-X=X-# (I)

where A represents an aryl group or a heteroaryl group, # represents a site where the group represented by formula (I) is attached to the carbon atom at the position 8 of the purine nucleus or the carbon atom at the position 5 or 6 of the pyrimidine nucleus, and two Xs, which are identical to or different from each other, each represents a nitrogen atom or CH whose H may be substituted by alkyl.

The group represented by the formula (I) can reversibly cause cis-trans isomerization of its double bond moiety upon receipt of light of two different wavelengths. Therefore, by introducing the group of interest into the base moiety of the nucleoside, it is possible to obtain a nucleoside compound capable of reversibly changing its structure upon irradiation with light. By introducing the nucleoside compound thus obtained at the aforementioned site of the RNA, it is possible to obtain an RNA capable of determining whether to bind to the factor involved in the initiation of translation in accordance with a structural change of the nucleoside compound.

More specifically, when the above-described RNA is in a cis form, the RNA can bind to the factor involved in the initiation of translation. On the other hand, when the above-described RNA is in a trans form, and the RNA cannot bind to the factor involved in the initiation of translation. That is, the RNA of the present invention causes reversible structural changes from a structure that enables the initiation of translation to a structure that disables the initiation of translation, and vice versa according to wavelengths of light with which the RNA is irradiated. Via the reversible structural changes, the present invention makes it possible to regulate the amount of protein produced by translation of the RNA of the present invention.

In the RNA according to the present invention, it is preferable that the nucleoside compound is introduced into the 5' cap structure. In such a case, the RNA according to the present invention, when it is in trans form, does not give rise to the binding with the translation initiation factor and therefore makes it possible to more reliably inhibit the initiation of the translation.

In the formula (I), it is preferable that both of the "X"s are nitrogen atoms. If the both of the "X"s are nitrogen atoms, the RNA according to the present invention can be reversibly isomerized by irradiation with visible light. The advantage of such a feature is that for in vivo regulation of the amount of protein produced by translation of the RNA according to the present invention which is introduced into a living body, there is no need to use ultraviolet light having harmful effects on the living body.

In the formula (I), in a case where X is CH, H may be substituted by alkyl. Alkyl as a substituent is alkyl having such a size as not to interfere cis-trans isomerization of the nucleoside compound. Such alkyl is, for example, $C_{1-5}$ alkyl, and preferably $C_{1-3}$ alkyl.

In cases where a certain functional group or a certain atom can have substituent(s), the type of the substituent(s), the number of substituent(s), and a position where substitution occurs are not particularly limited herein. Specific examples of the substituent include: a halogen atom (e.g. a fluorine atom, a chlorine atom, a bromine atom, and an iodine atom), aryl group (preferably a substituted or unsubstituted aryl group having 5 to 30 carbon atoms, for example, a phenyl group, a tolyl group, a xylyl group, a mesityl group, a biphenylyl group, a naphthyl group, anthryl group, a phenanthryl group, a fluorenyl group, and a pyrenyl group); a heteroaryl group (preferably a 5- to 10-membered ring heteroaryl group, for example, a pyrrolyl group, an imidazolyl group, an indolyl group, an indolyl group, a phenanthrolinyl group, a phenazinyl group, a thebenidinyl group, and a 10H-quindolinyl group); and an alkyl group (preferably a substituted or unsubstituted alkyl group having 1 to 20 carbon atoms, for example, a methyl group, an ethyl group, a propyl group, an isopropyl group, an n-butyl group, a sec-butyl group, a tert-butyl group, an n-pentyl group, a neopentyl group, a hexyl group, a heptyl group, an octyl group, a nonyl group, a decyl group, a undecyl group, a dodecyl group, a cyclopentyl group, a cyclohexyl group, a benzyl group, a phenethyl group, a diphenylmethyl group, and a trytyl group). Note that the term "carbon atoms" in a certain group means carbon atoms contained in a group having substituent(s), but excludes a carbon atom contained in the substituent(s).

In the present invention, the "nucleoside compound" includes a "purine nucleoside compound" and a "pyrimidine nucleoside compound". Among these nucleoside compounds, the "purine nucleoside compound" is a glycoside compound containing a purine nucleus, wherein a purine base is attached to a reducing group of a sugar by glycoside linkage. In the purine nucleoside compound of the present invention, the carbon atom at position 8 of the purine nucleus is substituted by the group represented by the formula (I) above. By isomerization of the double bond moiety, the purine nucleoside compound of the present invention takes either a trans isomer (left) or a cis isomer (right) shown as follows:

[Chem. 4]

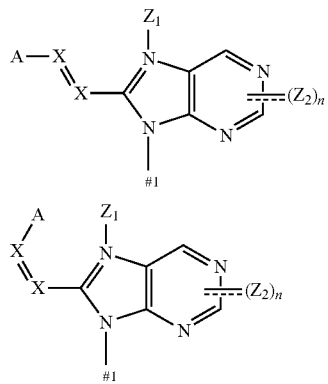

where $Z_1$ represents absence, a hydrogen atom, or a substituent, $Z_2$ represents a hydrogen atom or a substituent, n represents an integer ranging from 1 to 4, a double line formed by a solid line and a dashed line represents a single bond or a double bond, $\#_1$ represents a sugar attachment site, where n=2 or more, each $Z_2$ is identical or different from each other.

Here, in a case where the nucleoside compound is introduced into the 5' cap structure, examples of the substituent at 7-position of the purine nucleus include an aryl group, a heteroaryl group, an alkyl group, and a substituent attached to an aryl group or a heteroaryl group via an alkyl group. The aryl group is an aryl group having 6 to 30 carbon atoms, and more preferably an aryl group having 6 to 10 carbon atoms. The heteroaryl group is a 5- to 6-membered heteroaryl group, the alkyl group is an alkyl group having 1 to 6 carbon atoms in the form of a straight chain or a branched chain.

The substituent is more preferably a methyl group, but the nucleoside compound can be in a form where the substituent is absent.

In the chem. 4 and the formula (I), A represents an aryl group or a heteroaryl group. The aryl group has 5 to 30 carbon atoms, for example, and can be either monocyclic or polycyclic. The aryl group can have a substituent. Examples of the aryl group include a substituted or unsubstituted phenyl group and a substituted or unsubstituted naphthyl group. Further, non-limiting examples of the aryl group include: a phenyl group; an aryl group having 10 to 20 members forming a ring, such as a naphthyl group, an as-indacenyl group, an s-indacenyl group, an acenaphthylenyl group, a 9H-fluorenyl group, a phenanthryl group, an anthryl group, a fluoranthenyl group, an acephenanthrylenyl group, an aceanthrylenyl group, a triphenylenyl group, a pyrenyl group, a chrysenyl group, a tetraphenyl group, a naphthacenyl group, and a perylenyl group; and an aryl group having 21 to 30 members forming a ring, such as a picenyl group, a pentaphenyl group, and a pentacenyl group.

Among these aryl groups, an aryl group having 6 to 13 members that form a ring is preferable, and a substituted or unsubstituted naphthyl group is particularly preferable. For example, with "A" of such a group, synthesis of the RNA according to the present invention by transcription reaction brings about the following two effects:

(1) Transcription products (RNA according to the present invention) can be produced in high yields; and (2) Initiation of protein translation of the RNA according to the present invention and inhibition of the initiation can be regulated more appropriately by light irradiation.

Preferable from the viewpoint of the effect (1) is a monocyclic or bicyclic aryl group. Preferable from the viewpoint of the effect (2) is a bicyclic aryl group or an aryl group having a structure with three or more rings. Therefore, "A" can be selected as appropriate according to a yield of RNAs to be produced and an ease of the regulation of the amount of protein produced.

The heteroaryl group represented by "A" is exemplified by a 5- to 10-membered ring heteroaryl group containing, as ring-forming atom(s), one or more heteroatoms selected from the group consisting of a nitrogen atom, an oxygen atom, and a sulfur atom, and such a heteroaryl group can be either monocyclic or polycyclic, more preferably a 5- or 6-membered ring heteroaryl group containing, as the ring-forming atom(s), one or two nitrogen atoms, and further preferably a 5- or 6-membered ring heteroaryl group containing one nitrogen atom as the ring-forming atom. The heteroaryl group can have a substituent. Specific examples of the heteroaryl group include a monocyclic heteroaryl group having 5 or 6 members that form a ring containing a nitrogen atom as a heteroatom, such as a substituted or unsubstituted pyrrolyl group and an imidazolyl group; a condensed-ring heteroaryl group having 7 to 9 members that form a ring containing a nitrogen atom as a heteroatom, such as an indolyl group; and a heteroaryl group having 10 to 20 ring-forming atoms containing a nitrogen atom as a heteroatom, such as a quinolinyl group, a 2,7-naphthyridinyl group, a 2,6-naphthyridinyl group, a 1,6-naphthyridinyl group, a 1,5-naphthyridinyl group, a quinoxalinyl group, a quinazolinyl group, a cinnolinyl group, a 9H-carbazolyl group, a 9H-β-carbolinyl group, a phenanthridinyl group, a 1H-perimidinyl group, a phenanthrolinyl group, such as a 4,7-phenanthrolinyl group, a 3,8-phenanthrolinyl group, and a 2,9-phenanthrolinyl group, a phenazinyl group, a thebenidinyl group, and a 10H-quindolinyl group. Among these, a heteroaryl group having 5 to 10 ring-forming members is preferable.

Preferable examples of the purine nucleoside compound of the present invention include a guanosine derivative and an adenosine derivative both of which are represented by the following formulae. In the guanosine derivative and the adenosine derivative, the group represented by the formula (I) is attached to the 8-position carbon atom of the purine nucleus.

[Chem. 5]

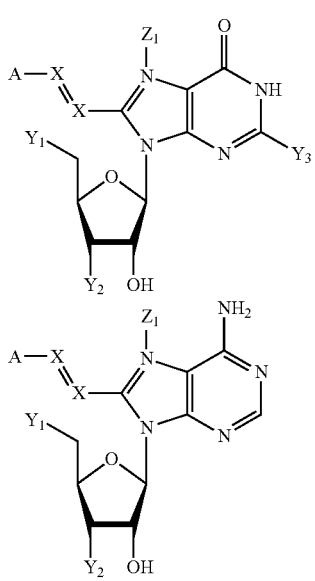

where the definitions and details of A and $Z_1$ are as described previously. Further, in the chem. 5, $Y_1$ is a hydroxyl group or —HPO$_3$—, $Y_2$ is —HPO$_3$—, and $Y_3$ represents a hydrogen atom, or a substituted or unsubstituted amino group or its protecting group. Examples of the protecting group include an isobutyl group and dimethylformamidine (DMF) group.

Regarding a method of synthesizing the purine nucleoside compound having an azo skeleton according to the present invention, see the section titled (Purine Nucleoside Compound) which will be described later. Further, regarding a method of synthesizing the purine nucleoside having an olefin skeleton, it should be referred to "Straightforward and Reversible Photoregulation of Hybridization using Photochromic Nucleoside" by S. Ogasawara and M. Maeda, Angew. Chem. Int. Ed. 2008, 47, 8839-8842 and "Reversible Photoswitching of a G-Quadruplex" by S. Ogasawara and M. Maeda, Angew. Chem. Int. Ed. 2009, 48, 6671-6674.

Further, it is possible to obtain the purine nucleoside compound represented by the formula (I), for example, by substituting, by the group represented by the formula (I), an 8-position halogen atom of a purine nucleoside derivative whose 8-position is halogenated (hereinafter referred to as "halogenated nucleoside derivative"). For example, an E-isomer can be synthesized by using Suzuki-Miyaura coupling. More specifically, a purine nucleus whose 8-position is halogenated and an (E)-alkenylboron compound are heated under reflux over several hours in the presence of a catalyst such as palladium. After a solvent is then removed therefrom by an evaporator, the reactant is subjected to purification using column purification, recrystallization, washing, and/or other method(s), and a target substance can be thereby obtained. For details of the above reaction, reference should be made to the descriptions in N. Miyaura et al., Chem. Rev., 1995, 95, 2457-2483; N. Amann et al., Synlett, 2002, 5, 687-691. On the other hand, an Z-isomer can be obtained, for example, by catalytic hydrogen reduction of 8-(arylethynyl)purine. The catalytic hydrogen reduction will be described more specifically. First, by using Sonogashira coupling, the purine nucleus whose 8-position is halogenated and an atomic group having a terminal alkyne are mixed simultaneously with a catalyst, such as palladium, as well as copper iodide, an amine base, and other(s), and the mixture is then heated under reflux over several hours. After the reaction, the solvent was removed by an evaporator, followed by purification using column purification, recrystallization, washing, and/or other method(s). The 8-(arylethynyl)purine thus obtained is solved in an adequate solvent, such as ethanol or methanol. After the system is purged with hydrogen in the presence of a catalyst such as palladium, the resulting solution is subjected to catalytic hydrogen reduction under normal pressure or under pressure.

Details of the synthesis reaction of the purine nucleoside compound of the present invention will be described later in Examples. Further, a material and a reagent used for the reaction can be synthesized by publicly known methods or can be commercially available products. The synthesis reaction can be followed by purification using publicly known methods as necessary, thereby to obtain a target substance. Obtaining of the target substance can be confirmed by NMR, mass spectrometry, or other identification method. It should be noted that the purine nucleoside compound represented by the formula (I) can form salt, depending upon the types of functional groups and substituents contained in the purine nucleoside compound, and can form solvate or hydrate in a free state or in a salt state. These forms of the purine nucleoside compound are also included in the scope of the invention.

As described previously, the RNA according to the present invention contains the 5' cap structure and the coding region having the 5' initiation codon and the 3' stop codon on both ends of the coding region. That is, the RNA according to the present invention contains the structure and region both required for translation in vitro or in vivo.

The RNA according to the present invention in which the nucleoside compound is introduced into the 5' cap structure can be synthesized, for example, by causing a given nucleoside to be attached to 5' carbon of the nucleoside compound through triphosphate bridge, and then undergoing transcription reaction by using a product thus obtained as a transcription primer. However, this method is a non-limiting method. Further, the RNA according to the present invention in which the nucleoside compound is introduced into any one of the 10 bases from the 5' end of the RNA can be synthesized, for example, by causing the 5' cap structure to be attached to a 5' end of an artificial oligonucleotide containing the nucleoside compound, and then undergoing transcription reaction by using a product thus obtained as a transcription primer.

The 5' cap structure can be given to the nucleoside compound or a given oligonucleotide by a publicly known enzyme (e.g. RNA polyphosphatase, RNA guanyl transferase, and guanine-7-methyl transferase). Further, the transcription reaction can be carried out by using, as a template, a DNA that codes a desired coding region and by using a publicly known RNA polymerase.

The 5' initiation codon of the RNA according to the present invention, which is a codon for initiating RNA transcription to a protein, is preferably AUG. However, the 5' initiation codon can be CUG, AUA, UUG, or others in exceptional cases, in view of the cases where translation of the RNA according to the present invention is made in an eubacterium. Further, the 3' stop codon of the RNA according to the present invention, which is a codon for terminating RNA transcription to a protein, can be selected as appropriate from UAA, UAG, and UGA.

The coding region of the RNA according to the present invention can be a region for coding for a desired protein the amount of which produced by translation is to be regulated.

The RNA according to the present invention may further contain a 5' noncoding region and/or a 3' noncoding region. The 5' noncoding region, which is inserted for the purpose of providing an appropriate distance between the 5' cap structure and the translational initiation codon, is not particularly limited as far as the 5' noncoding region has a length equal to or longer than 10 bases. The 5' noncoding region is preferably not more than 1000 bases long, more preferably not more than 900 bases long, further preferably not more than 800 bases long, still further preferably not more than 700 bases long, yet further preferably not more than 600 bases long, and further preferably not more than 500 bases long. It should be noted that in a case where there exists a 5' cap structure-independent translation initiation signal sequence such as Kozak sequence in the 5' noncoding region, translation starts regardless of the presence or absence of the 5' cap structure. Such a sequence is therefore removed if the nucleoside compound is introduced into the 5' cap structure. In a case where the nucleoside compound is introduced at a site selected from among the 10 bases from the 5' end of the RNA, such a sequence can be contained in the 5' noncoding region only as long as the sequence does not hinder the regulation of translational initiation by light irradiation. Further, the 5' noncoding region preferably contains at least either a sequence essential for binding of the RNA to an initiation factor or a ribosome complex or a sequence for increasing a translation efficiency.

The 3' noncoding region is not particularly limited as long as the 3' noncoding region has a length equal to or longer than 10 bases. Further, the 3' noncoding region preferably contains a sequence (polyA addition signal) for allowing a polyA sequence to be added at the 3' end of the 3' noncoding region. Non-limiting examples of the polyA addition signal include a base sequence of "AAUAAA", an SV40 early polyA signal containing two "AAUAAA" sequences, and a sequence having the SV40 early polyA signals arranged in tandem.

In addition, the RNA according to the present invention can contain a polyA sequence at the 3' end of the RNA. The RNA containing the polyA sequence at the 3' end thereof is superior in translation efficiency of a coding region and in RNA's own stability In the present invention, the "nucleoside compound" includes a "pyrimidine nucleoside compound", as described previously. The pyrimidine nucleoside compound is a pyrimidine nucleoside compound in which a 5- or 6-position carbon atom of a pyrimidine nucleus is substituted by the group represented by the formula (I) shown in the chem. 1.

The group represented by the formula (I) can reversibly cause cis-trans isomerization of a double bond moiety upon receipt of light of two different wavelengths. Therefore, by introducing the group of interest into the base moiety of the nucleoside, it is possible to obtain a nucleoside capable of reversibly changing its structure upon receipt of light.

The pyrimidine nucleoside compound is different from the aforementioned purine nucleoside compound in that a base moiety is a pyrimidine base. Therefore, the pyrimidine nucleoside compound is a glycoside compound containing a pyrimidine nucleus, wherein a pyrimidine base is attached to a reducing group of a sugar by glycoside linkage. Further, the "pyrimidine nucleus" is, for example, a thymine nucleus, a cytosine nucleus, or an uracil nucleus. In the pyrimidine nucleus, a 1-position nitrogen atom is attached to a sugar.

In a case where the pyrimidine nucleus is a thymine nucleus, the group represented by the formula (I) is attached to a 6-position carbon atom of the pyrimidine nucleus. Further, in a case where the pyrimidine nucleus is an uracil nucleus, it is preferable that the group represented by the formula (I) is attached to a 5-position carbon atom of the pyrimidine nucleus.

As described previously, the pyrimidine nucleoside compound has the same constitution as the aforementioned purine nucleoside compound, except for the base moiety. Therefore, for the definition of the symbol "A" in the formula (I), the structure of the sugar moiety to which the pyrimidine nucleus can be attached, the definitions of the terms, a synthesizing method, usage and advantage of the synthesizing method, etc., see, as necessary, the descriptions concerning the purine nucleoside compound.

[Method for Regulating the Amount of Protein Produced from RNA]

Further, the present invention relates to a method for regulating the amount of protein produced from the RNA, which has been described in the section titled [RNA According to the Present Invention]. This method includes a step of irradiating the RNA with first light and/or with second light, the first light having a wavelength to change a structure of a nucleoside compound from a trans form to a cis form by irradiation of the first light, the second light having a wavelength, which is different from that of the first light, to change the structure of the nucleoside compound from the cis form to the trans form by irradiation of the second light.

According to this method, irradiation of the RNA with the first light and/or the second light can initiate and/or stop the transcription of the RNA in vivo or in vitro. That is, the first light is light having a wavelength that causes isomerization from the trans form to the cis form to initiate the translation of the RNA. The second light is light having a wavelength that causes isomerization from the cis form to the trans form to inhibit the initiation of the RNA translation.

The above-described method further includes a step of introducing the RNA into a cell, and the step of irradiating is preferably a step of irradiating, with the first light and/or the second light, the cell into which the RNA is introduced. This makes it possible to regulate the amount of protein produced from the RNA in the cell.

Further, the above-described method is preferably such that the first light and the second light are irradiated in this order or in reverse order in the irradiation step. This makes it possible to reversibly switchably regulate initiation of the translation and inhibition of the initiation.

Still further, the above-described method is preferably such that the irradiation step is a step of irradiating, with the first light, a spot where the RNA is introduced in the cell. Yet further, the above-described method is preferably such that the light irradiation step is a step of simultaneously performing (i) the irradiation with the first light and (ii) irradiation of a region other than the spot with the second light. According to these arrangements, the RNAs located at the spot which have been irradiated with the first light, when spreading outside the spot with the passage of time, are subjected to the irradiation with the second light. That is, the initiation of translation of the RNAs having spread outside the spot are inhibited. Therefore, protein translation can be made from only the RNAs located at the spot.

The spot refers to a part of a cell (for example, approximately 5% to 10% of an area of an absorbed cell when the absorbed cell is viewed from above). More specifically, the spot refers to a region measuring approximately 1 μm to 5 μm in diameter.

Yet further, it is preferable that the above-described method is such that the irradiation with the first light is followed by irradiation of a region including the spot with the second light. This makes it possible to locally carry out reversible regulation of translation.

Further, the above-described method is preferably such that the first light and/or the second light is visible light. Ultraviolet light is harmful to a living cell or a living body. Therefore, it is preferable that the light for irradiation is visible light in carrying out the method according to the present invention with respect to a living cell or a living body. In a case where the method according to the present invention is carried out in vitro, the light for irradiation is visible light or ultraviolet light.

In a case where two Xs in the formula (I) are nitrogen atoms, the first light has a wavelength ranging from 400 nm to 500 nm, and the second light has a wavelength ranging from 450 nm to 600 nm. In this case, the first light is light always having a wavelength shorter than that of the second light. On the other hand, in a case where two Xs in the formula (I) are CH, the first light has a wavelength ranging from 300 nm to 500 nm, and the second light has a wavelength ranging from 240 nm to 400 nm. In this case, the first light is light always having a wavelength longer than that of the second light, which is contrary to the case where two Xs are nitrogen atoms. In addition, in a case where one of Xs is N and the other X is CH in the formula (I), the first light has a wavelength ranging from 300 nm to 500 nm, and the second light has a wavelength ranging from 240 nm to 450 nm. In this case, as in the case where two Xs are CH, the first light is light always having a wavelength longer than that of the second light.

Still further, the above-described method can realize isomerization of the RNA by means of two-photon excitation. The two-photon excitation occurs only on a substance situated in a focal plane, and thus makes it possible to realize RNA isomerization at a three-dimensional spot, i.e. to regulate initiation of the translation and inhibition of the initiation.

[Nucleoside Compounds According to the Present Invention]

(Purine Nucleoside Compound)

A purine nucleoside compound of the present invention is a purine nucleoside compound in which a 8-position carbon atom of a purine nucleus is substituted by a group represented by the following formula (I'):

[Chem. 6]

A-X=X-# (I')

where A represents an aryl group or a heteroaryl group, two Xs are nitrogen atoms, and # represents a site where the group represented by the following formula (I') is attached to the 8-position carbon atom of the purine nucleus.

The group represented by the formula (I') can reversibly cause cis-trans isomerization at its diazo moiety upon receipt of visible light of two different wavelengths. Therefore, by introducing the group of interest into the base moiety of the nucleoside, it is possible to obtain a nucleoside capable of reversibly changing its structure upon receipt of irradiation of visible light. Since the nucleoside of interest is capable of changing its structure upon receipt of visible light, there is no possibility that damage to a biomolecule (for example, protein and DNA, etc.) can occur when the nucleoside is introduced into a living cell. Since the base of interest is relatively small, a nucleotide chain into which the nucleoside is introduced can form a normal structure when structural change to one of the isomers occurs in the nucleoside.

The following will more specifically describe the purine nucleoside compound of the present invention.

In cases a certain functional group or a certain atom can have substituent(s), the type of the substituent(s), the number of substituent(s), and a position where substitution occurs are not particularly limited herein. Specific examples of the substituent include: a halogen atom (e.g. a fluorine atom, a chlorine atom, a bromine atom, and an isodine atom), aryl group (preferably a substituted or unsubstituted aryl group having 5 to 30 carbon atoms, for example, a phenyl group, a tolyl group, a xylyl group, a mesityl group, a biphenylyl group, a naphthyl group, anthryl group, a phenanthryl group, a fluorenyl group, and a pyrenyl group); a heteroaryl group (preferably a heteroaryl group having a 5- to 10-membered ring, for example, a pyrrolyl group, an imidazolyl group, an indolyl group, an indolyl group, a phenanthrolinyl group, a phenazinyl group, a thebenidinyl group, and 10H-quindolinyl group); and an alkyl group (preferably a substituted or unsubstituted alkyl group having 1 to 20 carbon atoms, for example, a methyl group, an ethyl group, a propyl group, an isopropyl group, an n-butyl group, a sec-butyl group, a tert-butyl group, an n-pentyl group, a neopentyl group, a hexyl group, a heptyl group, an octyl group, a nonyl group, a decyl group, a undecyl group, a dodecyl group, a cyclopentyl group, a cyclohexyl group, a benzyl group, a phenethyl group, a diphenylmethyl group, and a trytyl group). Note that the term "carbon atoms" in a certain group means carbon atoms contained in a group having substituent(s), but excludes a carbon atom contained in the substituent(s). This also applies to a pyrimidine nucleoside compound which will be described later.

In the present invention, the "purine nucleoside compound" is a glycoside compound containing a purine nucleus, wherein a purine base is attached to a reducing group of a sugar by glycoside linkage. Further, the "purine nucleus" in the present invention has the following structure:

[Chem. 7]

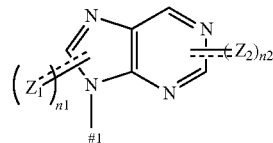

where $Z_1$ and $Z_2$ independently represents a hydrogen atom or a substituent, $n_1$ represents 1 or 2, $n_2$ represents an integer ranging from 1 to 4, a double line formed by a solid line and a dashed line represents a single bond or a double bond, $\#_1$ represents a sugar attachment site of a sugar, where $n_1=2$ and $n_2=2$ or more, each $Z_1$ is identical or different from each other and each $Z_2$ is identical or different from each other.

In the purine nucleoside compound of the present invention, the 8-position carbon atom of the purine nucleus is substituted by the group represented by the formula (I'). By isomerization of a diazo moiety, the purine nucleoside compound of the present invention takes either a trans form (E-isomer) or a cis form (Z-isomer) shown as follows:

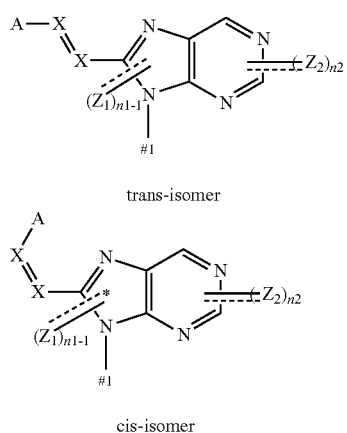

trans-isomer cis-isomer where $Z_1$, $Z_2$, $n_1$, $n_2$, $\#_1$, and a double line formed by a solid line and a dashed line are the same as those described previously.

In the chem. 7 and the formula (I'), A represents an aryl group or a heteroaryl group.

The aryl group has 5 to 30 carbon atoms, for example, and can be either monocyclic or polycyclic. The aryl group can have a substituent. Examples of the aryl group include a substituted or unsubstituted phenyl group and a substituted or unsubstituted naphthyl group. Further, non-limiting examples of the aryl group include: a phenyl group; an aryl group having 10 to 20 members forming a ring, such as a naphthyl group, an as-indacenyl group, an s-indacenyl group, an acenaphthylenyl group, a 9H-fluorenyl group, a phenanthryl group, an anthryl group, a fluoranthenyl group, an acephenanthrylenyl group, an aceanthrylenyl group, a triphenylenyl group, a pyrenyl group, a chrysenyl group, a tetraphenyl group, a naphthacenyl group, and a perylenyl group; and an aryl group having 21 to 30 members forming a ring, such as a picenyl group, a pentaphenyl group, and a pentacenyl group. The aryl group is preferably (i) an aryl group having 6 to 10 members forming a ring (ii) and a substituted or unsubstituted phenyl group. The substituted phenyl group is exemplified by a phenyl group having, as a substituent, a nitro group, a diethylamino group, a dimethylamino group, a trifluoromethyl group, a methoxy group, a carbonyl group, an electron-donating group such as halogen, or an electron-withdrawing group.

Among these groups, preferable are an aryl group having 6 to 10 members that form a ring and a substituted or unsubstituted phenyl group, more preferably a substituted or unsubstituted aryl group constituted by condensation of two rings and a substituted or unsubstituted phenyl group, and particularly preferably a methyl-substituted or unsubstituted phenyl group.

The heteroaryl group represented by "A" is exemplified by a 5- to 10-membered ring heteroaryl group containing, as ring-forming atom(s), one or more heteroatoms selected from the group consisting of a nitrogen atom, an oxygen atom, and a sulfur atom, and such a heteroaryl group can be either monocyclic or polycyclic, more preferably a 5- or 6-membered ring heteroaryl group containing, as the ring-forming atom(s), one or two nitrogen atoms, and further preferably a 5- or 6-membered ring heteroaryl group con-
taining one nitrogen atom as the ring-forming atom. The heteroaryl group can have a substituent. Specific examples of the heteroaryl group include a monocyclic heteroaryl group having 5 or 6 members that form a ring containing a nitrogen atom as a heteroatom, such as a substituted or unsubstituted pyrrolyl group and an imidazolyl group; a condensed-ring heteroaryl group having 7 to 9 members that form a ring containing a nitrogen atom as a heteroatom, such as an indolyl group; and a heteroaryl group having 10 to 20 ring-forming atoms containing a nitrogen atom as a heteroatom, such as a quinolinyl group, a 2,7-naphthyridinyl group, a 2,6-naphthyridinyl group, a 1,6-naphthyridinyl group, a 1,5-naphthyridinyl group, a quinoxalinyl group, a quinazolinyl group, a cinnolinyl group, a 9H-carbazolyl group, a 9H-β-carbolinyl group, a phenanthridinyl group, a 1H-perimidinyl group, a phenanthrolinyl group, such as a 4,7-phenanthrolinyl group, a 3,8-phenanthrolinyl group, and a 2,9-phenanthrolinyl group, a phenazinyl group, a thebenidinyl group, and a 10H-quindolinyl group. Among these, a heteroaryl group having 5 to 10 ring-forming members is preferable. Preferable examples of the heteroaryl group include the pyrrolyl group and the quinolinyl group.

Further, attachment sites of diazo linkage moieties in the aryl group and the heteroaryl group are not particularly limited and may be selected as appropriate according to what the group is and to a synthesizing method as used.

The group represented by the formula (I') is attached to the 8-position carbon atom of the purine nucleus at a site represented by $\#_1$ in the formula (I'). The structure of a sugar moiety attached by glycoside linkage in the purine nucleus where the substitution of the group represented by the formula (I') takes place is exemplified by, but is not particularly limited to, the structure of a sugar moiety contained in a publicly known nucleoside compound. More specifically, such a structure is exemplified by the structures of sugar moieties contained in the following formulae (II) and (III).

Preferable examples of the purine nucleoside compound of the present invention include a guanosine derivative represented by the following formula (II) and an adenosine derivative represented by the following formula (III). In the guanosine derivative and the adenosine derivative, the group represented by the above-described formula (I') is substituted for the 8-position carbon atom of the purine nucleus.

Note that the guanosine derivative represented by the formula (II) and the adenosine derivative represented by the formula (III) are trans forms; however, the purine nucleoside compound of the present invention is not limited to the trans form and can be a cis form.

[Chem. 9]

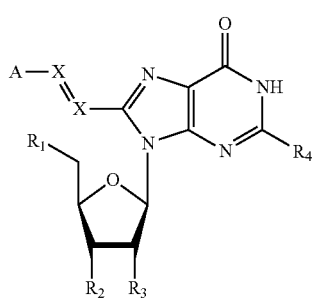

(II)

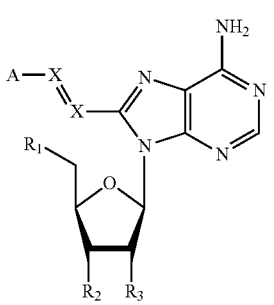

(III)

Definition and details of A in the formulae (II) and (III) are as described previously.

In the formulae (II) and (III), $R_1$ and $R_2$, which are independent from each other, each represents a hydroxyl group or its protective group, a reactive group that can be introduced for oligonucleotide production, or a atomic group that can be introduced in utilizing self-assembly of a nucleoside derivative.

$R_3$ represents a hydrogen group, a hydroxyl group or its protective group, a reactive group that can be introduced for oligonucleotide production, or an atomic group that can be introduced in utilizing self-assembly of a nucleoside derivative.

Examples of the protective group include isobutyl, tert-butyldimethylsilyl (TBDMS), and dimethoxytrityl (DMTr). Examples of the reactive group include 2-cyanoethyl-N,N,N',N'-tetraisopropylphosphoramidite, monophosphate, diphosphate, and triphosphate. Details of the atomic group are described in Isao Yoshikawa, et al., Tetrahedron 63 (2007) 7474-7481, Jeffery T. Davis, et al Chem. Soc. Rev., 2007, 36, 296-313, and Gian Piero Spada, et al., SYNLETT 2004, No. 4, pp 0596-0602. Specific examples of the atomic group include —OR (R is an alkylsilyl group (e.g. Si(iPr)$_2$C$_8$H$_{17}$) and an ester group. Further, at least two of $R_1$ through $R_3$ can be attached to each other to form a ring.

In the formulae (II) and (III), $R_4$ represents a hydrogen atom or a substituted or unsubstituted amino group or its protective group. Examples of the protective group include an isobutyl group and a dimethylformamidine (DMF) group.

Examples of a more specific form of the guanosine derivative represented by the formula (II) include the compounds represented by the following formulae (II)-1 and (II)-2. Examples of a more specific form of the adenosine derivative represented by the formula (III) include the compounds represented by the following formulae (III)-1 and (III)-2.

[Chem. 10]

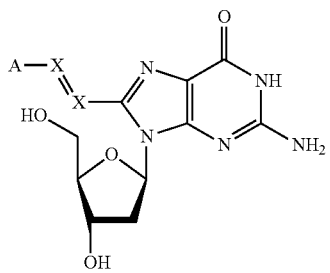

(II)-1

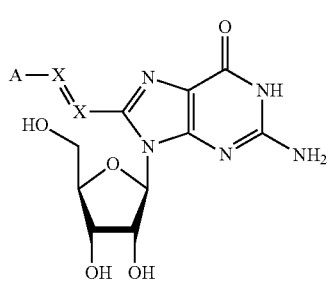

(II)-2

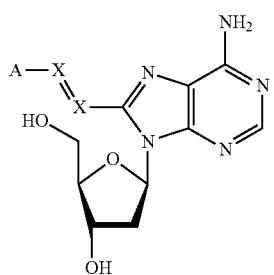

(III)-1

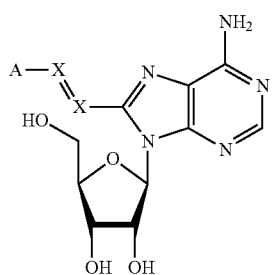

(III)-2 where A is the same as that described previously.

A method of synthesizing a purine nucleoside compound of the present invention is not particularly limited. By introducing the group represented by the formula (I') into a carbon at position 8 of a purine nucleoside by azo coupling using aniline, a purine nucleus, and nitrite, it is possible to obtain a purine nucleoside compound having the group represented by the formula (I'). For example, a mixture solution of aniline, a purine nucleus, and nitrite is heated under reflux for several hours, and after a solvent is then removed therefrom by an evaporator, the reactant is subjected to purification using column purification, recrystallization, washing, and/or other method(s), and a target substance can be thereby obtained.

Details of the synthesis reaction of the purine nucleoside compound of the present invention will be described later in Examples. Further, a material and a reagent used for the reaction can be synthesized by publicly known methods or can be commercially available products. The synthesis reaction can be followed by purification using publicly known methods as necessary, thereby to obtain a target substance. Obtaining of the target substance can be confirmed by NMR, mass spectrometry, or other identification method. It should be noted that the purine nucleoside compound represented by the formula (I') can form salt, depending upon the types of functional groups and substituents contained in the purine nucleoside compound, and can form solvate or hydrate in a free state or in a salt state. These forms of the purine nucleoside compound are also included in the scope of the invention.

The purine nucleoside compound of the present invention can reversibly regulate its structural change (isomerization). Further, since the purine nucleoside compound of the present invention changes its structure by a simple method of switching a light source on and off, the purine nucleoside compound of the present invention can be easily regulated in its structure.

Furthermore, it is also expected that the purine nucleoside compound of the present invention can be utilized for nucleic acid synthesis with use of an adequate polymerase. It is known that, in particular, a nitrogen atom at position 7 of a purine ring is involved in the interaction in a nucleic acid (hydrogen bond, coordinate bond to a metal ion, etc.). In a nucleic acid containing the purine nucleoside compound of the present invention, it is considered that inhibition of the above-described interaction can be regulated by trans to cis isomerization of the group represented by the formula (I') which has been substituted for the 8-position carbon atom of the purine ring, and it is expected that it becomes possible to regulate an activity of such a nucleic acid more accurately. In particular, introduction of a photoresponsive group into a base moiety has little influence on an entire molecular structure of the nucleic acid, and is therefore considered to be able to regulate the activity of the nucleic acid while maintaining the function of the nucleic acid. Further, the nucleic acid containing the purine nucleoside compound of the present invention is subjected to minimum modification and can therefore excellently form the conformations, such as double helix of DNA and RNA, a ribozyme, a deoxyribozyme, and an aptamer, without being influenced by the modification. Still further, the nucleic acid containing the purine nucleoside compound of the present invention can be easily introduced into a nucleic acid by a nucleic acid amplification technique such as PCR or RCA for the same reason.

(Pyrimidine Nucleoside Compound)

A pyrimidine nucleoside compound of the present invention is a pyrimidine nucleoside compound in which a 5- or 6-position carbon atom of a pyrimidine nucleus is substituted by a group represented by the formula (I') shown in the chem. 6.

The group represented by the formula (I') can reversibly cause cis-trans isomerization at its diazo moiety upon receipt of visible light of two different wavelengths. Therefore, by introducing the group of interest into the base moiety of the nucleoside, it is possible to obtain a nucleoside capable of reversibly changing its structure upon receipt of irradiation of visible light. Since the nucleoside of interest is capable of changing its structure upon receipt of visible light, there is no possibility that damage to a biomolecule (for example, protein, DNA, etc.) can occur when the nucleoside is introduced into a living cell. Since the base of interest is relatively small, a nucleotide chain into which the nucleoside is introduced can form a normal structure when structural change to one of the isomers occurs in the nucleoside.

The pyrimidine nucleoside compound is different from the aforementioned purine nucleoside compound in that a base moiety is a pyrimidine base. Therefore, the pyrimidine nucleoside compound of the present invention is a glycoside compound containing a pyrimidine nucleus, wherein a pyrimidine base is attached to a reducing group of a sugar by glycoside linkage. Further, the "pyrimidine nucleus" in the present invention is, for example, a thymine nucleus, a cytosine nucleus, or an uracil nucleus. In the pyrimidine nucleus in the present invention, a 1-position nitrogen atom is attached to a sugar.

In a case where the pyrimidine nucleus is a thymine nucleus, the group represented by the formula (I') is attached to a 6-position carbon atom of the pyrimidine nucleus. Further, in a case where the pyrimidine nucleus is a cytosine nucleus or an uracil nucleus, it is preferable that the group represented by the formula (I') is attached to a 5-position carbon atom of the pyrimidine nucleus.

As described previously, the pyrimidine nucleoside compound of the present invention has the same constitution as the aforementioned purine nucleoside compound, except for the base moiety. Therefore, for the definition of the symbol "A" in the formula (I'), the structure of the sugar moiety to which the pyrimidine nucleus can be attached, the definitions of the terms, a synthesizing method, usage and advantage of the synthesizing method, etc., reference should be made as necessary to the descriptions in the section titled (Purine Nucleoside Compound).

[Isomerization Method and Method of Changing Optical Properties]

Still further, the present invention relates to (i) a method of irradiating the nucleoside compound of the present invention with visible light to isomerize the nucleoside compound and (ii) a method of irradiating the nucleoside compound of the present invention with visible light to change optical properties of the nucleoside compound.

As described previously, the nucleoside compound of the present invention can reversibly cause cis-trans isomerization of the diazo moiety in the group represented by the formula (I). The nucleoside compound of the present invention is such that both the trans form and the cis form have high stability. Thus, in the nucleoside compound of the present invention, the isomerization does not proceed unless light irradiation is not carried out, and it is possible to regulate the isomerization (trans to cis isomerization and cis to trans isomerization) by light irradiation. The trans to cis isomerization can be caused by irradiation of the trans form with visible light of a medium wavelength (e.g. wavelength ranging from 400 nm to 500 nm). The cis to trans isomerization can be caused by irradiation of the cis form with visible light of a wavelength (e.g. wavelength ranging from 450 nm to 600 nm) longer than the wavelength of the light used for the trans to cis isomerization. Further, in a case where A in the formula (I) is a phenyl group or a phenyl group having a substituent, the trans to cis isomerization is caused by irradiation with visible light ranging from 400 nm to 450 nm, and the cis to trans isomerization is caused by irradiation with visible light ranging from 500 nm to 600 nm. Both the trans to cis isomerization and the cis to trans isomerization can easily proceed at room temperature. Moreover, conditions for isomerization, such as s duration of the light irradiation for the isomerization, a light source to be used, and an intensity of the irradiation light, may be determined as appropriate. For the conditions for the isomerization, reference should also be made to the Examples which will be described later.

The nucleoside compound of the present invention is such that the trans form and the cis form are different from each other in optical properties such as absorption spectrum and quantum yield. Therefore, the isomerization by visible light irradiation can change optical properties of the nucleoside compound of the present invention. Moreover, since the photoisomerization can be reversibly caused, alternate irradiations of the nucleoside compound of the present invention with visible light of different wavelength can reversibly change the optical properties of the compound. The conditions of light irradiation for change of the optical properties are as described above.

[Optical Switching-Type Device Material]

Yet further, the present invention relates to an optical switching-type device material that includes a nucleic acid containing the nucleoside compound of the present invention or that includes the nucleoside compound of the present invention. The optical switching-type device material of the present invention can be constituted by at least one of the nucleoside compounds or at least one of the nucleic acids, or the optical switching-type device material of the present invention can contain other components normally used in an electronic device.

In the present invention, the term "optical switching-type" refers to a property of being functionally and structurally switchable upon irradiation with visible light. As described previously, the nucleoside compound of the present invention can be reversibly isomerized by irradiation with visible light to change its structure and can change its optical property accordingly. By taking advantage of such a property, the following can be realized. For example, the state of the trans form can be set to be "ON" or "1" as a binary digit of a digital signal, while the state of the cis form can be set to be "OFF" or "0" as a binary digit of a digital signal. With this configuration, it is possible to form an electronic device such as a switching element or a storage element. In particular, the optical switching-type device material of the present invention is suitable as an optical switch for a light-driven nanodevice.

[Method for Reversibly Photoregulating Function of Functional Nucleic Acid]

By introducing the nucleoside compound of the present invention into a given DNA or RNA by using a DNA/RNA automated synthesizer or an enzyme such as polymerase, functions of a functional nucleic acid, such as an antisense, an aptamer, and a ribozyme, can be reversibly photoregulated. For example, it is possible to reversibly photoregulate RNA interference (RNAi) by introducing the nucleoside compound of the present invention into an oligonucleotide with about 20 bases so that formation of a double helix with a target RNA is regulated.

EXAMPLES

Example 1

(1-1) Synthesis of Nucleoside Compound Having Olefin Skeleton

[Chem. 11]

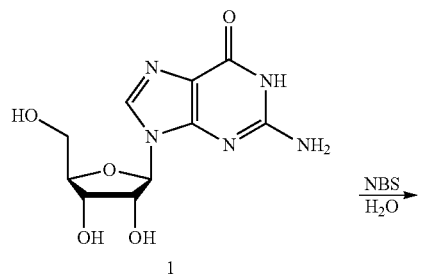

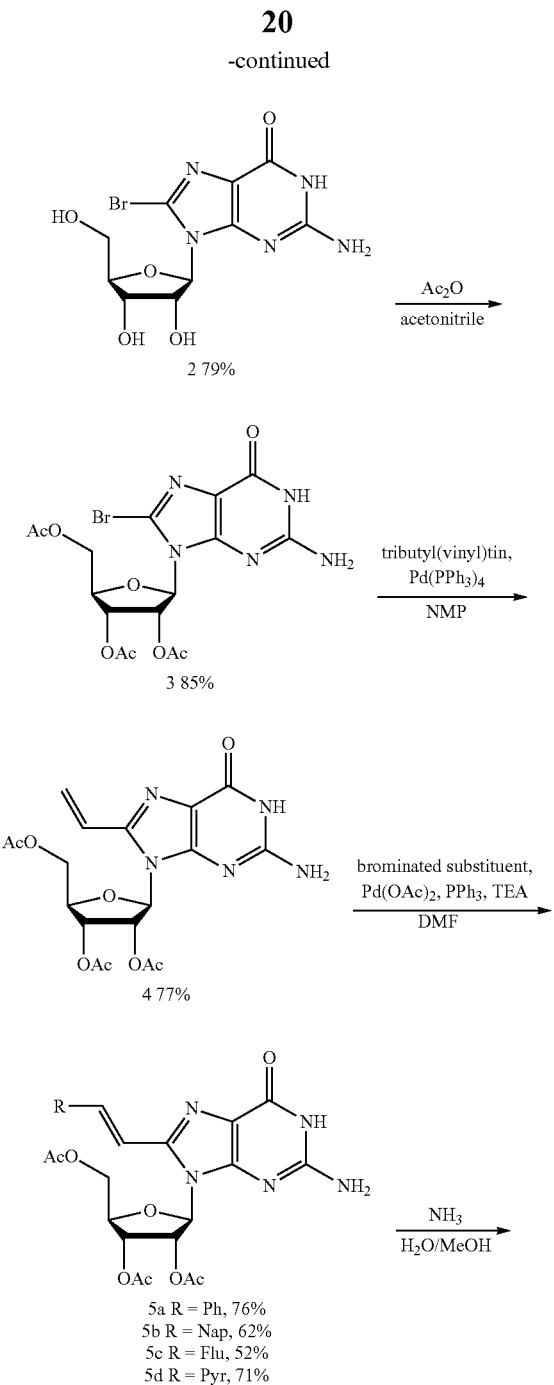

5a R = Ph, 76%
5b R = Nap, 62%
5c R = Flu, 52%
5d R = Pyr, 71%

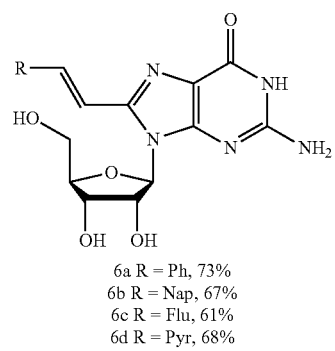

6a R = Ph, 73%
6b R = Nap, 67%
6c R = Flu, 61%
6d R = Pyr, 68%

(1-1-1) Synthesis of 8-Styrylguanosine (Reference Numeral 6a of the Chem. 11)

Ten grams of guanosine (reference numeral 1 in the chem. 11), 7.54 g of N-bromosuccinimide, and 500 mL of water were placed in an eggplant-shaped flask, and the mixture solution thus prepared was stirred for 2 hours at room temperature. After the reaction, resultant precipitate was filtered off to obtain 9.03 g of 8-bromoguanosine (reference numeral 2 in the chem. 11).

The 9.03 g of 8-bromoguanosine (reference numeral 2 in the chem. 11) thus obtained was placed in a two-necked eggplant-shaped flask, and nitrogen purging of the flask under reduced pressure was repeated three times so that the system was thoroughly purged with nitrogen. To the 9.03 g of 8-bromoguanosine were added 100 mL of acetonitrile, 76 mg of dimethylaminopyridine, 9.46 mL of acetic anhydride, and 13.9 mL of triethylamine. The mixture solution thus prepared was stirred for 1.5 hours at room temperature. After removal of the solvent from the resulting solution on a rotary evaporator, the residue was recrystallized in water to obtain 10.3 g of 8-bromo-2',3',5'-tri-O-acetylguanosine (reference numeral 3 in the chem. 11).

In a two-necked eggplant-shaped flask, 2.5 g of 8-bromo-2',3',5'-tri-O-acetylguanosine (reference numeral 3 in the chem. 11) and 10 mL of N-methylpyrrolidone were introduced. The mixture solution thus prepared was then bubbled with argon gas for 10 minutes. Next, 593 mg of tetrakis (triphenylphosphine) palladium and 2.99 mL of tributyl (vinyl)tin were added thereto, and the system was purged with argon, after which the mixture solution was heated under reflux for 1 hour at 110° C. After the solvent was then removed therefrom using a rotary evaporator, the reactant was subjected to purification by silica gel chromatography (dichloromethane:methanol=95:5). Fractions containing the target substance were collected, and the eluent was then removed from the fractions to obtain 1.71 g of 8-vinyl-2',3',5'-tri-O-acetylguanosine (reference numeral 4 in the chem. 11).

In a two-necked eggplant-shaped flask, 257 mg of triphenylphosphine was placed, and nitrogen purging of the flask under reduced pressure was repeated three times so that the system was thoroughly purged with nitrogen. To the 257 mg of triphenylphosphine were added 20 mL of dioxane, 88 mg of palladium (II) acetate, and 0.812 mL of triethylamine. The mixture solution thus prepared was stirred for 10 minutes at 60° C. After it was confirmed that the reaction solution was discolored wine red, 0.614 mL of bromobenzene, 1.7 g of 8-vinyl-2',3',5'-tri-O-acetylguanosine (reference numeral 4 in the chem. 11) dissolved in 20 mL of DMF were added in this order to the reaction solution, and the mixture solution was heated under reflux for 1 hour at 115° C. From the resulting solution, the catalyst was removed by filtration, and the solvent was then removed by using a rotary evaporator. After that, purification was carried out by silica gel chromatography (chloroform:methanol=95:5). Fractions containing the target substance were collected, and the eluent was then removed from the fractions to obtain 1.51 g of 8-styryl-2',3',5'-tri-O-acetylguanosine (reference numeral 5a in the chem. 11).

The 1.51 g of 8-styryl-2',3',5'-tri-O-acetylguanosine (reference numeral 5a in the chem. 11) thus obtained was placed in a two-necked eggplant-shaped flask, and nitrogen purging of the flask under reduced pressure was repeated three times so that the system was thoroughly purged with nitrogen. To the 1.51 g of 8-styryl-2',3',5'-tri-O-acetylguanosine were added 25 mL of methanol and 25 mL of 2M ammonia (methanol solution). The mixture solution thus prepared was stirred for 4 hours at 60° C. Resultant precipitate was collected from the resulting solution to obtain 830 mg of styrylguanosine (reference numeral 6a in the chem. 11).

(1-1-2) Synthesis of 8-Naphthylvinylguanosine (Reference Numeral 6b in the Chem. 11)

In a two-necked eggplant-shaped flask, 257 mg of triphenylphosphine was placed, and nitrogen purging of the flask under reduced pressure was repeated three times so that the system was thoroughly purged with nitrogen. To the 257 mg of triphenylphosphine were added 20 mL of dioxane, 88 mg of palladium (II) acetate, and 0.812 mL of triethylamine. The mixture solution thus prepared was stirred for 10 minutes at 60° C. After it was confirmed that the reaction solution was discolored wine red, 1.21 g of bromonaphthalene dissolved in 10 mL of DMF and 1.7 g of 8-vinyl-2',3',5'-tri-O-acetylguanosine (reference numeral 4 in the chem. 11) dissolved in 10 mL of DMF were added in this order to the reaction solution, and the mixture solution was heated under reflux for 1 hour at 115° C. From the resulting solution, the catalyst was removed by filtration, and the solvent was then removed by using a rotary evaporator. After that, purification was carried out by silica gel chromatography (chloroform:methanol=95:5). Fractions containing the target substance were collected, and the eluent was then removed from the fractions to obtain 1.37 g of 8-naphthylvinyl-2',3',5'-tri-O-acetylguanosine (reference numeral 5b in the chem. 11).

The 1.36 g of 8-naphthylvinyl-2',3',5'-tri-O-acetylguanosine (reference numeral 5b in the chem. 11) was placed in a two-necked eggplant-shaped flask, and nitrogen purging of the flask under reduced pressure was repeated three times so that the system was thoroughly purged with nitrogen. To the 1.36 g of 8-naphthylvinyl-2',3',5'-tri-O-acetylguanosine were added 20 mL of methanol and 20 mL of 2M ammonia (methanol solution). The mixture solution thus prepared was stirred for 4 hours at 60° C. Resultant precipitate was collected from the resulting solution to obtain 710 mg of 8-naphthylvinylguanosine (reference numeral 6b in the chem. 11).

(1-1-3) Synthesis of 8-Fluorenylvinylguanosine (Reference Numeral 6c in the Chem. 11)

In a two-necked eggplant-shaped flask, 257 mg of triphenylphosphine was placed, and nitrogen purging of the flask under reduced pressure was repeated three times so that the system was thoroughly purged with nitrogen. To the 257 mg of triphenylphosphine were added 20 mL of dioxane, 88 mg of palladium (II) acetate, and 0.812 mL of triethylamine. The mixture solution thus prepared was stirred for 10 minutes at 60° C. After it was confirmed that the reaction solution was discolored wine red, 1.44 g of bromofluorene dissolved in 10 mL of DMF and 1.7 g of 8-vinyl-2',3',5'-tri-O-acetylguanosine (reference numeral 4 in the chem. 11) dissolved in 10 mL of DMF were added in this order to the reaction solution, and the mixture solution was heated under reflux for 1 hour at 115° C. From the resulting solution, the catalyst was removed by filtration, and the solvent was then removed using a rotary evaporator. After that, purification was carried out by silica gel chromatography (chloroform:methanol=95:5). Fractions containing the target substance were collected, and the eluent was then removed from the fractions to obtain 1.23 g of 8-fluorenylvinyl-2',3',5'-tri-O-acetylguanosine (reference numeral 5c in the chem. 11).

The 1.22 g of 8-fluorenylvinyl-2',3',5'-tri-β-acetylguanosine (reference numeral 5c in the chem. 11) was placed in a two-necked eggplant-shaped flask, and nitrogen purging of the flask under reduced pressure was repeated three times so that the system was thoroughly purged with nitrogen. To the 1.22 g of 8-fluorenylvinyl-2',3',5'-tri-β-acetylguanosine were added 20 mL of methanol and 20 mL of 2M ammonia (methanol solution). The mixture solution thus prepared was stirred for 4 hours at 60° C. Resultant precipitate was collected from the resulting solution to obtain 590 mg of 8-fluorenylvinylguanosine (reference numeral 6c in the chem. 11).

(1-1-4) Synthesis of 8-Pyrenylvinylguanosine (Reference Numeral 6d in the Chem. 11)

In a two-necked eggplant-shaped flask, 257 mg of triphenylphosphine was placed, and nitrogen purging of the flask under reduced pressure was repeated three times so that the system was thoroughly purged with nitrogen. To the 257 mg of triphenylphosphine were added 20 mL of dioxane, 88 mg of palladium (II) acetate, and 0.812 mL of triethylamine. The mixture solution thus prepared was stirred for 10 minutes at 60° C. After it was confirmed that the reaction solution was discolored wine red, 1.65 g of bromopyrene dissolved in 15 mL of DMF and 1.7 g of 8-vinyl-2',3',5'-tri-O-acetylguanosine (reference numeral 4 in the chem. 11) dissolved in 10 mL of DMF were added in this order to the reaction solution, and the mixture solution was heated under reflux for 1 hour at 115° C. From the resulting solution, the catalyst was removed by filtration, and the solvent was then removed using a rotary evaporator. After that, purification was carried out by silica gel chromatography (chloroform:methanol=95:5). Fractions containing the target substance were collected, and the eluent was then removed from the fractions to obtain 1.76 g of 8-pyrenylvinyl-2',3',5'-tri-O-acetylguanosine (reference numeral 5d in the chemical formula II).

The 1.76 g of 8-pyrenylvinyl-2',3',5'-tri-O-acetylguanosine (reference numeral 5d in the chem. 11) was placed in a two-necked eggplant-shaped flask, and nitrogen purging of the flask under reduced pressure was repeated three times so that the system was thoroughly purged with nitrogen. To the 1.76 g of 8-pyrenylvinyl-2',3',5'-tri-O-acetylguanosine were added 25 mL of methanol and 25 mL of 2M ammonia (methanol solution). The mixture solution thus prepared was stirred for 4 hours at 60° C. Resultant precipitate was collected from the resulting solution to obtain 962 mg of 8-pyrenylvinylguanosine (reference numeral 6d in the chem. 11).

(1-1-5) Synthesis of 8-Styryl-Guanosine Triphosphate

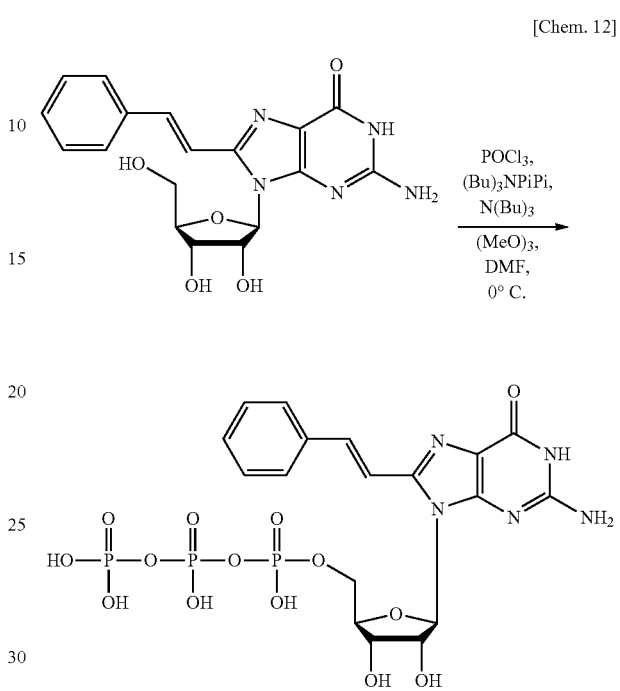

[Chem. 12]

In a two-necked eggplant-shaped flask, 109 mg of 8-styrylguanosine (reference numeral 6a in the chem. 11) was placed, and nitrogen purging of the flask under reduced pressure was repeated three times so that the system was thoroughly purged with nitrogen. To the 109 mg of 8-styrylguanosine were added 1 mL of trimethyl phosphate and 91 mg of proton sponge. After that, the mixture solution thus prepared was cooled to 0° C. Next, the mixture solution was mixed with 31 μL of phosphoryl chloride, and stirred at 0° C. After 6 hours of stirring, the resulting solution was mixed with 269 μL of tributylamine and 250 mg of tributyl ammonium pyrophosphate. The mixture solution was further stirred for 1 minute. The resulting solution was mixed with 37 mL of 1M TEAB buffer solution to stop the reaction. Thereafter, purification was carried out using DEAE Sephadex (0M to 1M TEAB). Fractions containing the target substance were collected, and the solvent was then removed from the fractions to obtain 8-styryl-guanosine triphosphate (TEA salt). After that, the 8-styryl-guanosine triphosphate thus obtained was converted into free acids by using a weak anion exchange column (Strata-X-AW, SHIGMA Co.) to obtain 7.2 mg of 8-styryl-guanosine triphosphate (represented by chem. 12) that is the target compound.

$^1$H NMR (D$_2$O, 400 MHz) δ: 7.31-7.22 (m, 6H), 6.83 (d, J=16.1, 1H), 5.93 (d, J=6.4, 1H), 5.17 (t, J=5.8, 1H), 4.51 (s, 1H), 4.24-4.14 (m, 3H); $^{31}$P NMR (D$_2$O, 400 MHz) δ: −16.5 (2P), −28.4 (1P); ESI-TOF MS (M-H)$^-$ for C$_{18}$H$_{22}$N$_5$O$_{14}$P$_3$, Calculated: 624.0298. Found: 624.0070.

(1-2) Synthesis of 5' Nucleoside Including 5' Cap Structure Having Olefin Skeleton

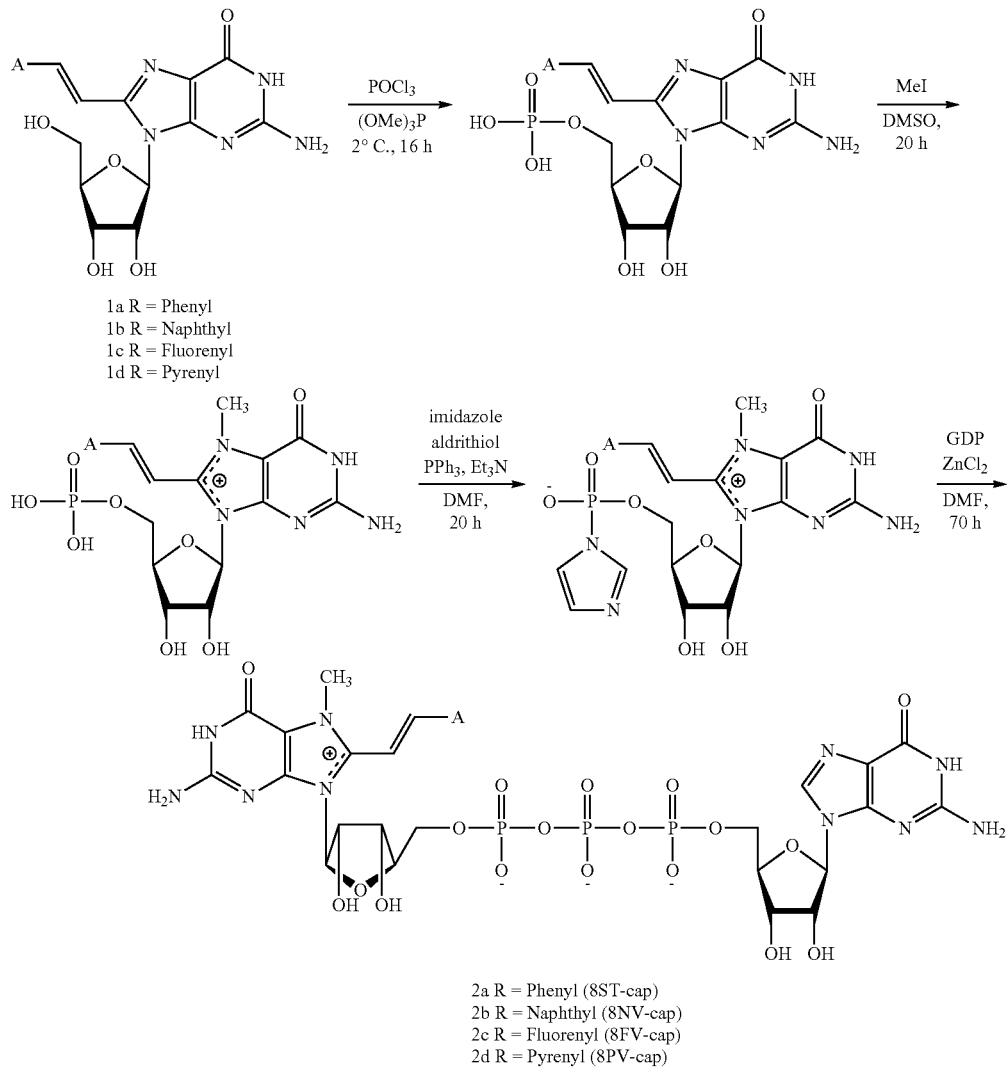

[Chem. 13]

2a R = Phenyl (8ST-cap)
2b R = Naphthyl (8NV-cap)
2c R = Fluorenyl (8FV-cap)
2d R = Pyrenyl (8PV-cap)

(2-1) Synthesis of 5' Nucleoside (8ST-Cap, Reference Numeral 2a in Chem. 13) Including 8-Styrylvinylguanosine as 5' Cap Structure In a two-necked eggplant-shaped flask, 870 mg of 8-styrylvinylguanosine (reference numeral 1a in the chem. 13) was placed, and nitrogen purging of the flask under reduced pressure was repeated three times so that the system was thoroughly purged with nitrogen. In the two-necked eggplant-shaped flask, 13 mL of trimethyl phosphate and 0.412 mL of phosphoryl chloride were additionally placed. The mixture solution thus prepared was stirred for 20 hours at 2° C. Thereafter, 20 mL of water was further added to the resulting solution, and 1M TEAB buffer solution was then added to the resulting solution to adjust pH of the reaction solution to 5.5. Resultant precipitate was collected and then washed with water, after which the precipitate was dried thoroughly in a desiccator. Monophosphate thus obtained was placed in a two-necked eggplant-shaped flask, and nitrogen purging of the flask under reduced pressure was repeated three times so that the system was thoroughly purged with nitrogen. In the two-necked eggplant-shaped flask, 25 mL of DMSO and 2 mL of methyl iodide were additionally placed. The mixture solution was stirred overnight at room temperature. To the reaction solution was added 100 mL of cold water, after which resultant precipitate was collected and then washed with methanol. Thus obtained monophosphate methylated at position 7 was placed in a two-necked eggplant-shaped flask, and nitrogen purging of the flask under reduced pressure was repeated three times so that the system was thoroughly purged with nitrogen. In the two-necked eggplant-shaped flask were additionally placed 10 mL of DMF, 340 mg of imidazole, 524 mg of triphenylphosphine, 440 mg of aldrithiol, and 0.554 mL of triethylamine. The mixture solution thus prepared was stirred overnight at room temperature. The reaction solution was poured into an acetone solution in which 450 mg of sodium perchlorate was dissolved, and the resulting solution was stirred for 2 hours at 4° C. Resultant precipitate was collected and then washed with cold acetone, after which the precipitate was dried thoroughly in a desiccator. A compound thus obtained and 268 mg of GDP were placed in a two-necked eggplant-shaped flask, and nitrogen purging of the flask under reduced pressure was repeated three times so that the system was thoroughly purged with nitrogen. In the two-necked eggplant-shaped flask, 20 mL of DMF and 308 mg of zinc chloride were additionally placed. The mixture solution thus prepared was stirred for 60 hours at room temperature. The reaction solution thus obtained was poured into an aqueous solution in which 1.48 g of EDTA was dissolved, and 1M TEAB buffer solution was then added to the resulting solution to adjust pH of the reaction solution to 5.5. Then, purification was carried out using DEAE Sephadex (0M to 1M TAEB buffer solution). Fractions containing the target substance were collected, and the solvent was then removed from the fractions. After that, 8ST-cap (TEA salt) thus obtained was exchanged into free acids by using a weak anion exchange column (Strata-X-AW, SHIGMA Co.) to obtain 103 mg of 8ST-cap (reference numeral 2a in the chem. 13) that is the target compound.

TABLE 1

$^1$H NMR (D$_2$O, 400 MHz) δ: 7.90 (s, 1H), 7.52 (d, J = 5.0, 2H), 7.34 (s, 3H), 7.26 (d, J = 16.6, 1H), 6.91 (d, J = 16.6, 1H), 5.88 (d, J = 5.8, 1H), 5.64 (d, J = 5.8, 1H), 5.26 (t, J = 5.6, 1H), 4.61 (t, J = 4.1, 1H), 4.56 (t, J = 5.6, 1H), 4.39-4.29 (m, 3H), 4.25-4.10 (m, 4H), 3.99 (s, 3H); $^{31}$P NMR (D$_2$O, 400 MHz) δ: −11.5 (2P, α, γ), −23.1 (1P, β); FAB MS (M − H)$^-$ for C$_{29}$H$_{35}$N$_{10}$O$_{18}$P$_3$, Calculated: 903.13; Found: 903.69.

(1-2-2) Synthesis of 5' Nucleoside (8NV-Cap, Reference Numeral 2b in the Chem. 13) Including 8-Naphthylvinylguanosine as 5' Cap Structure In a two-necked eggplant-shaped flask, 700 mg of 8-styrylvinylguanosine (reference numeral 1b in the chem. 13) was placed, and nitrogen purging of the flask under reduced pressure was repeated three times so that the system was thoroughly purged with nitrogen. In the two-necked eggplant-shaped flask, 9 mL of trimethyl phosphate and 0.294 mL of phosphoryl chloride were additionally placed. The mixture solution thus prepared was stirred for 20 hours at 2° C. Thereafter, 20 mL of water was further added to the resulting solution, and 1M TEAS buffer solution was then added to the resulting solution to adjust pH of the reaction solution to 5.5. Resultant precipitate was collected and then washed with water, after which the precipitate was dried thoroughly in a desiccator. Monophosphate thus obtained was placed in a two-necked eggplant-shaped flask, and nitrogen purging of the flask under reduced pressure was repeated three times so that the system was thoroughly purged with nitrogen. In the two-necked eggplant-shaped flask, 25 mL of dimethyl sulfoxide (DMSO) and 1.74 mL of methyl iodide were additionally placed. The mixture solution was stirred overnight at room temperature. To the reaction solution was added 100 mL of cold water, after which Resultant precipitate was collected and then washed with methanol. Thus obtained monophosphate methylated at position 7 was placed in a two-necked eggplant-shaped flask, and nitrogen purging of the flask under reduced pressure was repeated three times so that the system was thoroughly purged with nitrogen. In the two-necked eggplant-shaped flask were additionally placed 10 mL of N,N-dimethylformamide (DMF), 308 mg of imidazole, 476 mg of triphenylphosphine, 401 mg of aldrithiol, and 0.501 mL of triethylamine. The mixture solution thus prepared was stirred overnight at room temperature. The reaction solution was poured into an acetone solution in which 401 mg of sodium perchlorate was dissolved, and the resulting solution was stirred for 2 hours at 4° C. Resultant precipitate was collected and then washed with cold acetone, after which the precipitate was dried thoroughly in a desiccator. A compound thus obtained and 715 mg of GDP were placed in a two-necked eggplant-shaped flask, and nitrogen purging of the flask under reduced pressure was repeated three times so that the system was thoroughly purged with nitrogen. In the two-necked eggplant-shaped flask, 25 mL of DMF and 455 mg of zinc chloride were additionally placed. The mixture solution thus prepared was stirred for 60 hours at room temperature. The reaction solution thus obtained was poured into an aqueous solution in which 2.19 g of EDTA was dissolved, and 1M TEAB buffer solution was then added to the resulting solution to adjust pH of the reaction solution to 5.5. Then, purification was carried out using DEAE Sephadex (0M to 1M TAEB buffer solution). Fractions containing the target substance were collected, and the solvent was then removed from the fractions. After that, 8NV-cap (TEA salt) thus obtained was exchanged into free acids by using a weak anion exchange column (Strata-X-AW, SHIGMA Co.) to obtain 92 mg of 8NV-cap (reference numeral 2b in the chem. 13) that is the target compound.

TABLE 2

$^1$H NMR (D$_2$O, 300 MHz) δ: 8.06 (s, 1H), 7.52-7.32 (m, 7H), 7.06 (d, J = 16.1, 1H), 6.51 (d, J = 16.1, 1H), 5.56 (d, J = 2.8, 1H), 5.44 (d, J = 3.7, 1H), 5.09 (t, J = 5.1, 1H), 4.56 (t, J = 5.1, 1H), 4.36-4.34 (m, 4H), 4.23-4.08 (m, 4H), 3.42 (s, 3H); $^{31}$P NMR (D$_2$O, 400 MHz) δ: −11.4 (2P, α, γ), −23.1 (1P, β); FAB MS (M − H)$^-$ for C$_{33}$H$_{37}$N$_{10}$O$_{18}$P$_3$, Calculated: 953.14; Found: 953.23.

(1-2-3) Synthesis of 5' Nucleoside (8FV-Cap, Reference Numeral 2c in the Chem. 13) Including 8-Fluorenylvinylguanosine as 5' Cap Structure In a two-necked eggplant-shaped flask, 580 mg of 8-fluorenylvinylguanosine (reference numeral 1b in the chem. 13) was placed, and nitrogen purging of the flask under reduced pressure was repeated three times so that the system was thoroughly purged with nitrogen. In the two-necked eggplant-shaped flask, 13 mL of trimethyl phosphate and 0.224 mL of phosphoryl chloride were additionally placed. The mixture solution thus prepared was stirred for 20 hours at 2° C. Thereafter, 10 mL of water was further added to the resulting solution, and 1M TEAB buffer solution was then added to the resulting solution to adjust pH of the reaction solution to 5.5. Resultant precipitate was collected and then washed with water, after which the precipitate was dried thoroughly in a desiccator. Monophosphate thus obtained was placed in a two-necked eggplant-shaped flask, and nitrogen purging of the flask under reduced pressure was repeated three times so that the system was thoroughly purged with nitrogen. In the two-necked eggplant-shaped flask, 20 mL of DMSO and 0.9 mL of methyl iodide were additionally placed. The mixture solution was stirred overnight at room temperature. To the reaction solution was added 100 mL of cold water, after which resultant precipitate was collected and then washed with methanol. Thus obtained monophosphate methylated at position 7 was placed in a two-necked eggplant-shaped flask, and nitrogen purging of the flask under reduced pressure was repeated three times so that the system was thoroughly purged with nitrogen. In the two-necked eggplant-shaped flask were additionally placed 5 mL of DMF, 120 mg of imidazole, 185 mg of triphenylphosphine, 155 mg of aldrithiol, and 0.196 mL of triethylamine. The mixture solution thus prepared was stirred overnight at room temperature. The reaction solution was poured into an acetone solution in which 150 mg of sodium perchlorate was dissolved, and the resulting solution was stirred for 2 hours at 4° C. Resultant precipitate was collected and then washed with cold acetone, after which the precipitate was dried thoroughly in a desiccator. A compound thus obtained and 395 mg of GDP were placed in a two-necked eggplant-shaped flask, and nitrogen purging of the flask under reduced pressure was repeated three times so that the system was thoroughly purged with nitrogen. In the two-necked eggplant-shaped flask, 15 mL of DMF and 250 mg of zinc chloride were additionally placed. The mixture solution thus prepared was stirred for 60 hours at room temperature. The reaction solution thus obtained was poured into an aqueous solution in which 1.23 g of EDTA was dissolved, and 1M TEAB buffer solution was then added to the resulting solution to adjust pH of the reaction solution to 5.5. Then, purification was carried out using DEAE Sephadex (0M to 1M TAEB buffer solution). Fractions containing the target substance were collected, and the solvent was then removed from the fractions. After that, 8FV-cap (TEA salt) thus obtained was exchanged into free acids by using a weak anion exchange column (Strata-X-AW, SHIGMA Co.) to obtain 85 mg of SFV-cap (reference numeral 2c in the chem. 13) that is the target compound.

TABLE 3

$^1$H NMR (D$_2$O, 400 MHz) δ: 8.26 (s, 1H), 7.94-7.48 (m, 7H), 7.29 (d, J = 16.1, 1H), 6.73 (d, J = 16.1, 1H), 5.92 (d, J = 4.4, 1H), 5.82 (d, J = 5.4, 1H), 5.52 (t, J = 5.1, 1H), 4.89-4.37 (m, 9H), 3.94 (s, 3H), 3.83 (s, 3H); $^{31}$P NMR (D$_2$O, 400 MHz) δ: −11.4 (2P, α, γ), −23.0 (1P, β); FAB MS (M − H)$^-$ for C$_{36}$H$_{39}$N$_{10}$O$_{18}$P$_3$, Calculated: 991.16; Found: 991.17.

(1-2-4) Synthesis of 5' Nucleoside (8PV-Cap, Reference Numeral 2d in the Chem. 13) Including 8-Fluorenylvinylguanosine as 5' Cap Structure In a two-necked eggplant-shaped flask, 900 mg of 8-pyrenylvinylguanosine (reference numeral 1b in the chem. 13) was placed, and nitrogen purging of the flask under reduced pressure was repeated three times so that the system was thoroughly purged with nitrogen. In the two-necked eggplant-shaped flask, 10 mL of trimethyl phosphate and 0.194 mL of phosphoryl chloride were additionally placed. The mixture solution thus prepared was stirred for 20 hours at 2° C. Thereafter, 20 mL of water was further added to the resulting solution, and 1M TEAB buffer solution was then added to the resulting solution to adjust pH of the reaction solution to 5.5. Resultant precipitate was collected and then washed with water, after which the precipitate was dried thoroughly in a desiccator. Monophosphate thus obtained was placed in a two-necked eggplant-shaped flask, and nitrogen purging of the flask under reduced pressure was repeated three times so that the system was thoroughly purged with nitrogen. In the two-necked eggplant-shaped flask, 40 mL of DMSO and 2.96 mL of methyl iodide were additionally placed. The mixture solution thus prepared was stirred overnight at room temperature. To the reaction solution was added 100 mL of cold water, after which resultant precipitate was collected and then washed with methanol. Thus obtained monophosphate methylated at position 7 was placed in a two-necked eggplant-shaped flask, and nitrogen purging of the flask under reduced pressure was repeated three times so that the system was thoroughly purged with nitrogen. In the two-necked eggplant-shaped flask were additionally placed 20 mL of DMF, 575 mg of imidazole, 887 mg of triphenylphosphine, 745 mg of aldrithiol, and 0.936 mL of triethylamine. The mixture solution thus prepared was stirred overnight at room temperature. The reaction solution was poured into an acetone solution in which 750 mg of sodium perchlorate was dissolved, and the resulting solution was stirred for 2 hours at 4° C. Resultant precipitate was collected and then washed with cold acetone, after which the precipitate was dried thoroughly in a desiccator. A compound thus obtained and 760 mg of GDP were placed in a two-necked eggplant-shaped flask, and nitrogen purging of the flask under reduced pressure was repeated three times so that the system was thoroughly purged with nitrogen. In the two-necked eggplant-shaped flask, 45 mL of DMF and 876 mg of zinc chloride were additionally introduced. The mixture solution thus obtained was stirred for 60 hours at room temperature. The reaction solution thus obtained was poured into an aqueous solution in which 4.21 g of EDTA was dissolved, and 1M TEAB buffer solution was then added to the resulting solution to adjust pH of the reaction solution to 5.5. Then, purification was carried out using DEAE Sephadex (0M to 1M TAEB buffer solution). Fractions containing the target substance were collected, and the solvent was then removed from the fractions. After that, 8PV-cap (TEA salt) thus obtained was exchanged into free acids by using a weak anion exchange column (Strata-X-AW, SHIGMA Co.) to obtain 87 mg of 8PT-cap (reference numeral 2d in the chem. 13) that is the target compound.

TABLE 4

$^1$H NMR (D$_2$O, 400 MHz) δ: 8.48-7.82 (m, 9H), 7.31 (d, J = 12.2, 1H), 7.08 (d, J = 12.2, 1H), 6.37 (d, J = 5.8, 1H), 5.81 (d, J = 5.8, 1H), 5.44 (t, J = 5.4, 1H), 4.99-4.39 (m, 9H), 2.92 (s, 3H); $^{31}$P NMR (D$_2$O, 400 MHz) δ: −12.0 (2P, α, γ), −23.5 (1P, β); FAB MS (M − H)$^-$ for C$_{39}$H$_{39}$N$_{10}$O$_{18}$P$_3$, Calculated: 1027.16; Found: 1027.32.

(1-3) Protein Translation of RNA Containing Photoresponsive 5' Cap (Four types of) GFP-coding RNAs containing the respective photoresponsive 5' caps which had been synthesized in (1-2) were synthesized by using a cell-free transcription kit (MEGAscript, Ambion Co.). By using a cell-free protein translation system (Transdirect dinsect cell, SIGMA Co.), GFPs were synthesized from the respective RNAs. In addition, GFP-coding mRNAs (with or without the cap structure) were used as comparative controls. The expression levels of GFPs from the respective RNAs were compared in fluorescence intensity of the GFPs. For the RNAs containing the photoresponsive 5' caps, the expression level of GFP was also compared between the cis form and the trans form (shown in the upper part of FIG. 1). The results are shown in FIG. 1. In FIG. 1, "no-cap" denotes mRNA with no cap structure, "normal-cap" denotes normal mRNA with the cap structure.

As shown in FIG. 1 (in the lower part), the RNAs containing the photoresponsive 5' caps in the cis forms exhibited higher expression levels, as compared to the RNAs in the trans forms. Among these RNAs, the RNA containing the 8NV-cap in the trans form expressed almost no protein, but the RNA containing the 8NV-cap in the cis form exhibited the expression level that is equal to the normal-cap's expression level. It can therefore be said that the 8NV-cap in the photoresponsive 5' caps exhibited an excellent property. Note that data concerning the RNA containing the 8PV-cap is not shown in FIG. 1. Since the 8PV-cap has a high hydrophobicity, it was highly likely that the 8PV-cap was not introduced into mRNA. Therefore, it was impossible to determine whether the result of the translation regulation test concerning the RNA containing the 8PV-cap had been obtained by the action of the nucleoside compound according to the present invention.

Figure 2:
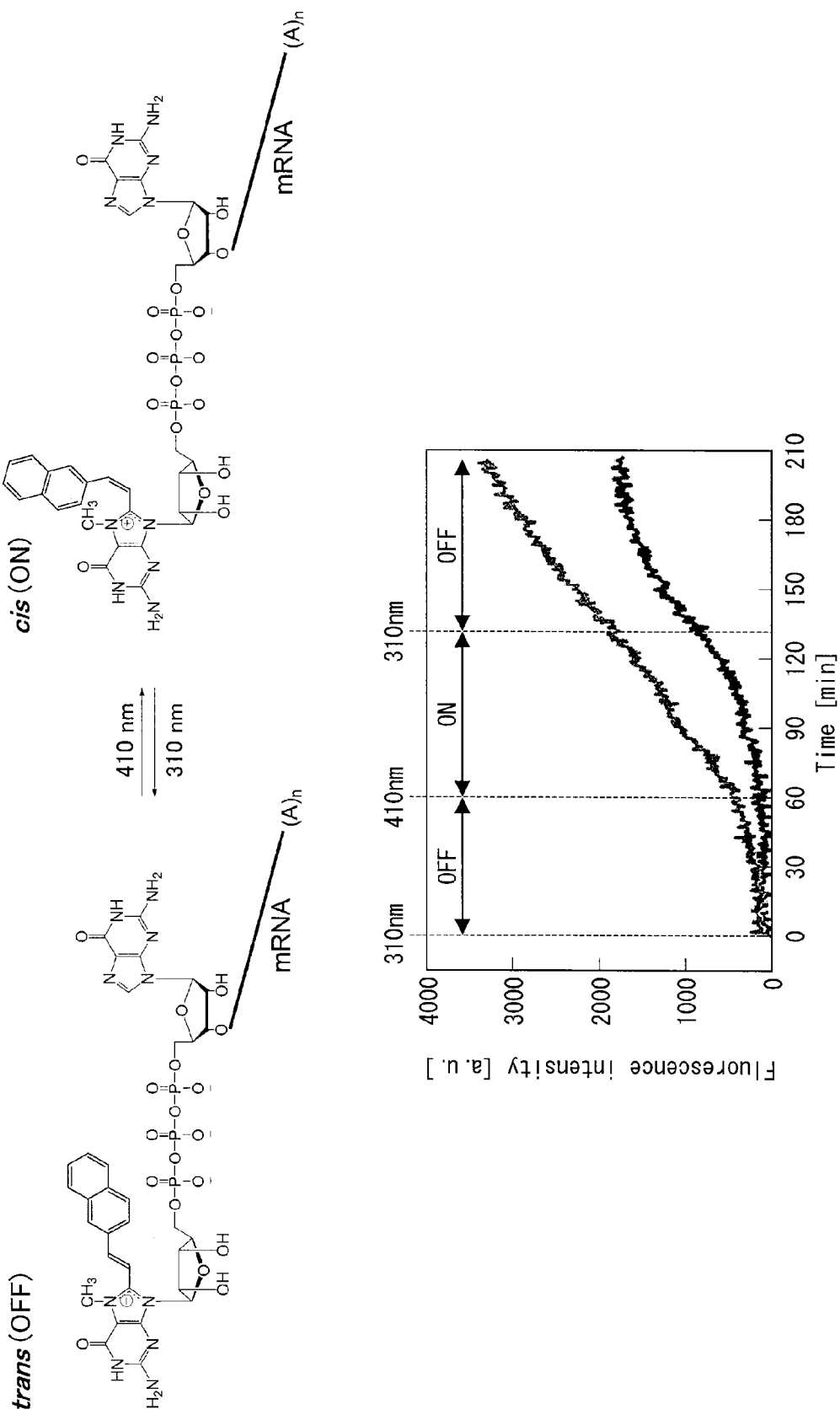
FIG. 2 is a view proving in vitro regulation of translation of a GFP-coding RNA according to the present invention by irradiation with light having different wavelengths and fluorescence intensity of the GFP.

(1-4) Reversible Photoregulation of Protein Translation of the RNA Containing the Photoresponsive 5' Cap Protein translation of the RNA containing the 8NV-cap by using the cell-free protein translation system (Transdirect dinsect cell, SIGMA Co.) was reversibly photoregulated in the following manner. As a comparative control, the normal-cap was used. First, reaction solution systems were irradiated with light of 310 nm for 2 minutes (the 8NV-cap was turned into the trans form). Sixty minutes after the irradiation with light of 310 nm, the reaction solution systems were irradiated with light of 410 nm for 2 minutes (the 8NV-cap was turned into the cis form). Another 60 minutes after the irradiation with light of 410 nm, the reaction solution systems were irradiated with light of 310 nm for 2 minutes (the 8NV-cap was turned into the trans form). FIG. 2 shows the time course of fluorescence intensity of GFPs (in the lower part of FIG. 2) at this time and the structures of the RNA containing the 8NV-cap (in the upper part of FIG. 2).

As shown in FIG. 2 (in the lower part), during the first 60 minutes, the fluorescence intensity of GFP was constant, and the expression of GFP from the RNA containing the 8NV-cap was not confirmed (lower graph). In the subsequent period, increase in fluorescence intensity of GFP was confirmed. This confirmed the expression of GFP from the RNA containing the 8NV-cap. In the further subsequent period, the fluorescence intensity of GFP mildly increased and then stayed at a fixed value. This conformed that the expression of GFP from the RNA containing the 8NV-cap was stopped. On the contrary, in the case of the normal-cap, the increase in fluorescence intensity of GFP, which indicates the expression of GFP, was constantly confirmed. As described above, protein translation of the RNA (8NV-cap) according to the present Example was repeatedly stopped and initiated in a reversible manner by alternate irradiation of light beams of two different wavelengths.

Example 2

(2-1) Synthesis of Nucleoside Compound Having Azo Skeleton (2-1-1) Synthesis of 8-(4-Methoxyphenyl)Azoguanosine (Reference Numeral 5 in Chem. 14)

[Chem. 14]

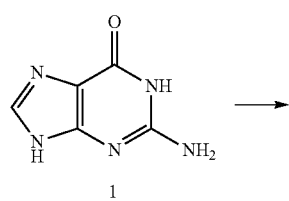

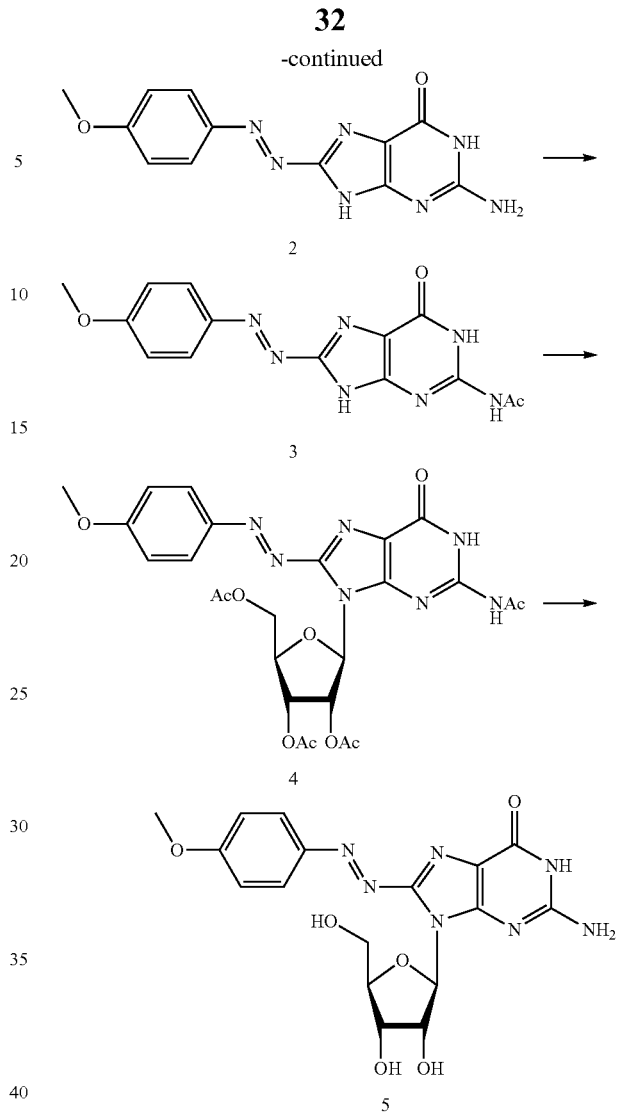

Solution 1 was prepared by adding 37% by weight of hydrochloric acid (12 mL) and 1.48 g of p-anisidine to 60 mL of water while cooling. Then, 3.0 g of guanosine was dissolved in 1.5% by weight of NaOH aqueous solution (600 mL), and the resulting solution was cooled in an ice bath. To the ice bath were added $NaNO_2$ (828 mg) aqueous solution and the solution 1, and the mixture solution was stirred for 30 minutes at 0° C. After the reaction, a reactant was precipitated by addition of acetic acid and was allowed to stand for 2 hours. A deposit precipitated was collected by filtration to obtain 3.73 g of 8-(4-methoxyphenyl)azoguanine (reference numeral 2 in the chem. 14).

The 3.73 g of 8-(4-methoxyphenyl)azoguanine thus obtained was placed in a two-necked eggplant-shaped flask, and nitrogen purging of the flask under reduced pressure was repeated three times so that the system was thoroughly purged with nitrogen. In the two-necked eggplant-shaped flask, 60 mL of DMA and 2.47 mL of acetic anhydride were additionally placed, and the mixture solution thus prepared was heated under reflux for 2 hours at 160° C. After the reaction, a deposit was collected by filtration and then washed with methanol to obtain 2.88 g of 2-N-acetyl-8-(4-methoxyphenyl)azoguanine (reference numeral 3 in the chem. 14).

In a two-necked eggplant-shaped flask, 2.30 g of 2-N-acetyl-8-(4-methoxyphenyl)azoguanine was placed, and nitrogen purging of the flask under reduced pressure was repeated three times so that the system was thoroughly purged with nitrogen. In the two-necked eggplant-shaped flask, 70 mL of dichloroethane and 12.4 mL of N,O-bis(trimethylsilyl)acetamide were additionally placed, and the mixture solution thus prepared was heated under reflux for 1 hour at 80° C. After the reaction, the solvent was removed by using a rotary evaporator. Nitrogen purging of the flask containing a reactant under reduced pressure was repeated three times so that the system was thoroughly purged with nitrogen. In the flask were additionally placed 70 mL of toluene, 1.53 mL of trimethylsilyl trifluoromethanesulfonic acid, and 2.69 g of β-D-ribofuranose-1,2,3,5-tetraacetate, and the mixture solution thus prepared was heated under reflux for 2 hours at 80° C. After the solvent was then removed therefrom by using a rotary evaporator, the reactant was subjected to purification by silica gel chromatography (chloroform:methanol=95:5). Fractions containing the target substance were collected, and the eluent was then removed from the fractions to obtain 804 mg of 2',3',5'-O-acetyl-2-N-acetyl-8-(4-methoxyphenyl)azoguanosine (reference numeral 4 in the chem. 14).

In a two-necked eggplant-shaped flask, 800 mg of 2',3',5'-O-acetyl-2-N-acetyl-8-(4-methoxyphenyl) azoguanosine was placed, and nitrogen purging of the flask under reduced pressure was repeated three times so that the system was thoroughly purged with nitrogen. In the two-necked eggplant-shaped flask, 12 mL of methanol and 15 mL of ammonia (methanol solution) were additionally placed, and the mixture solution thus prepared was stirred for 6 hours at 60° C. After the reaction, a deposit was collected by filtration and then washed with methanol to obtain 462 mg of 8-(4-methoxyphenyl)azoguanosine (reference numeral 5 in the chem. 14).

(2-1-2) Synthesis of 8-(4-Aminoquinolyl)Azoguanosine (Reference Numeral 5 in the Chem. 15)

[Chem. 15]

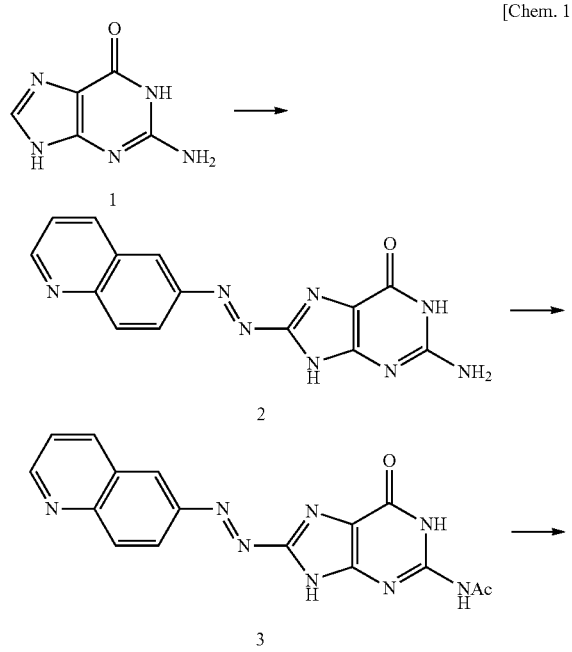

-continued

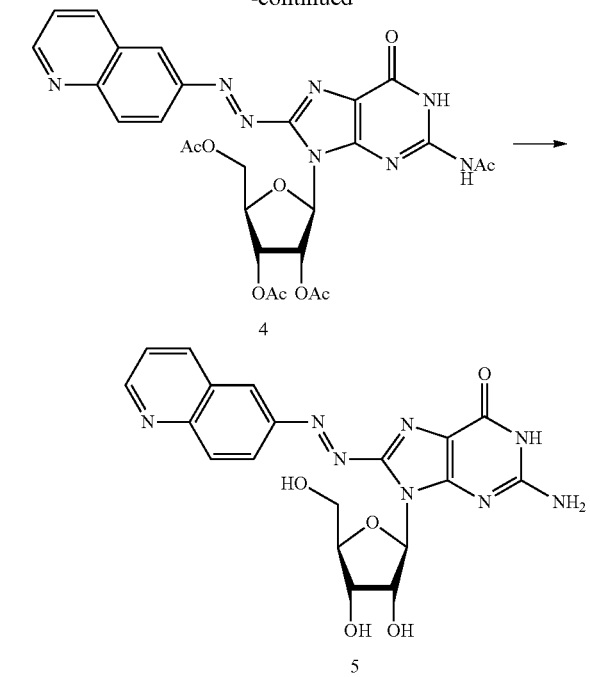

Solution 2 was prepared by adding 37% by weight of hydrochloric acid (6 mL) and 1.00 g of aminoquinoline to 30 mL of water while cooling. Then, 1.74 g of guanosine was dissolved in 1.5° AD by weight of NaOH aqueous solution (300 mL), and the resulting solution was cooled in an ice bath. To the ice bath were added NaNO₂ (479 mg) aqueous solution and the solution 2, and the mixture solution was stirred for 30 minutes at 0° C. After the reaction, a reactant was precipitated by addition of acetic acid and was allowed to stand for 2 hours. A deposit precipitated was collected by filtration to obtain 2.23 g of 8-(6-aminoquinolyl)azoguanine (reference numeral 2 in the chem. 15).

In a two-necked eggplant-shaped flask, 2.15 g of 8-(6-aminoquinolyl)azoguanine was placed, and nitrogen purging of the flask under reduced pressure was repeated three times so that the system was thoroughly purged with nitrogen. In the two-necked eggplant-shaped flask, 50 mL of DMA and 1.79 mL of acetic anhydride were additionally placed, and the mixture solution thus prepared was heated under reflux for 2 hours at 160° C. After the reaction, a deposit was collected by filtration and then washed with methanol to obtain 1.85 g of 2-N-acetyl-8-(6-aminoquinolyl)azoguanine (reference numeral 3 in the chem. 15).

In a two-necked eggplant-shaped flask, 1.85 g of 2-N-acetyl-8-(6-aminoquinolyl)azoguanine was placed, and nitrogen purging of the flask under reduced pressure was repeated three times so that the system was thoroughly purged with nitrogen. In the two-necked eggplant-shaped flask, 70 mL of dichloroethane and 9.6 mL of N,O-bis(trimethylsilyl)acetamide were additionally placed, and the mixture solution thus prepared was heated under reflux for 1 hour at 80° C. After the reaction, the solvent was removed by using a rotary evaporator. Nitrogen purging of the flask containing a reactant under reduced pressure was repeated three times so that the system was thoroughly purged with nitrogen. In the flask were additionally placed 70 mL of toluene, 1.19 mL of trimethylsilyl trifluoromethanesulfonic acid, and 2.10 g of β-D-ribofuranose-1,2,3,5-tetraacetate, and the mixture solution thus prepared was heated under reflux for 2 hours at 80° C. After the solvent was then removed therefrom by using a rotary evaporator, the reactant was subjected to purification by silica gel chromatography (chloroform:methanol=95:5). Fractions containing the target substance were collected, and the eluent was then removed from the fractions to obtain 300 mg of 2',3',5'-O-acetyl-2-N-acetyl-8-(6-aminoquinolyl)azoguanosine (reference numeral 4 in the chem. 15).

In a two-necked eggplant-shaped flask, 300 mg of 2',3',5'-O-acetyl-2-N-acetyl-8-(6-aminoquinolyl)azoguanosine was placed, and nitrogen purging of the flask under reduced pressure was repeated three times so that the system was thoroughly purged with nitrogen. In the two-necked eggplant-shaped flask, 4 mL of methanol and 6 mL of ammonia (methanol solution) were additionally placed, and the mixture solution thus prepared was stirred for 6 hours at 60° C. After the reaction, a deposit was collected by filtration and then washed with methanol to obtain 186 mg of 8-(6-aminoquinolyl)azoguanosine (reference numeral 5 in the chem. 15).

(2-1-3) Synthesis of
8-(4-Ethylphenyl)Azoguanosine (Reference
Numeral 5 in Chem. 16)

[Chem. 16]

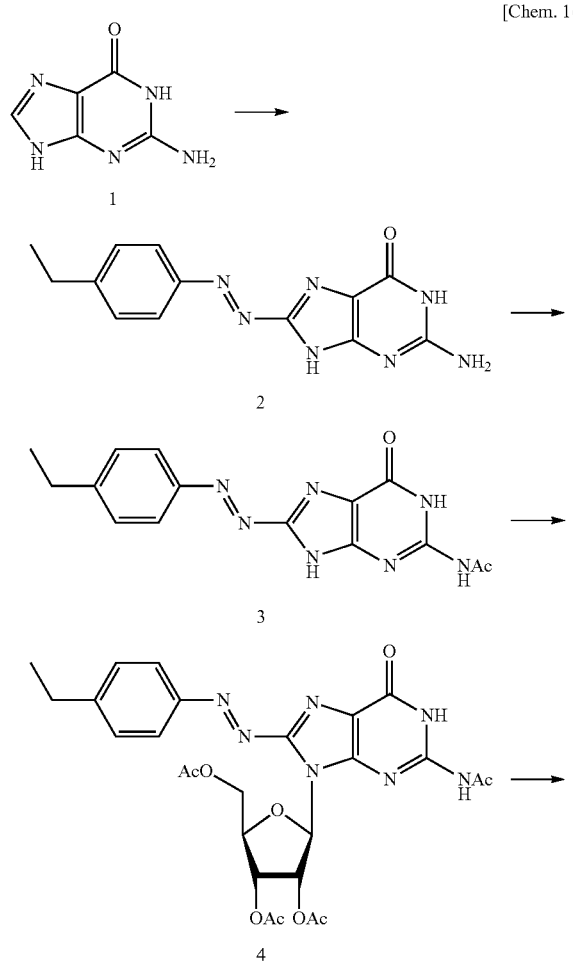

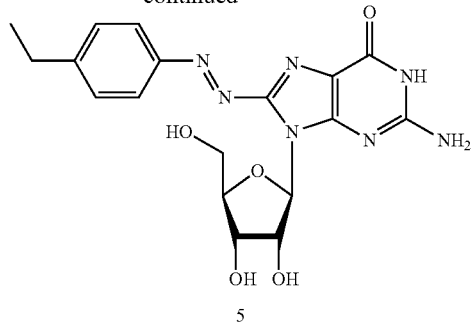

Solution 3 was prepared by adding 37% by weight of hydrochloric acid (12 mL) and 1.50 mL of 4-ethylaniline to 60 mL of water while cooling. Then, 3.00 g of guanosine was dissolved in 1.5% by weight of NaOH aqueous solution (600 mL), and the resulting solution was cooled in an ice bath. To the ice bath were added $NaNO_2$ (828 mg) aqueous solution and the solution 3, and the mixture solution was stirred for 30 minutes at 0° C. After the reaction, a reactant was precipitated by addition of acetic acid and was allowed to stand for 2 hours. A deposit precipitated was collected by filtration to obtain 3.84 g of 8-(4-ethylphenyl)azoguanine (reference numeral 2 in the chem. 16).

The 3.84 g of 8-(4-ethylphenyl)azoguanine thus obtained was placed in a two-necked eggplant-shaped flask, and nitrogen purging of the flask under reduced pressure was repeated three times so that the system was thoroughly purged with nitrogen. In the two-necked eggplant-shaped flask, 60 mL of DMA and 2.56 mL of acetic anhydride were additionally placed, and the mixture solution thus prepared was heated under reflux for 2 hours at 160° C. After the reaction, a deposit was collected by filtration and then washed with methanol to obtain 2.82 g of 2-N-acetyl-8-(4-ethylphenyl)azoguanine (reference numeral 3 in the chem. 16).

In a two-necked eggplant-shaped flask, 2.38 g of 2-N-acetyl-8-(4-ethylphenyl)azoguanine was placed, and nitrogen purging of the flask under reduced pressure was repeated three times so that the system was thoroughly purged with nitrogen. In the two-necked eggplant-shaped flask, 65 mL of dichloroethane and 13.1 mL of N,O-bis(trimethylsilyl)acetamide were additionally placed, and the mixture solution thus prepared was heated under reflux for 30 minutes at 80° C. After the reaction, the solvent was removed by using a rotary evaporator. Nitrogen purging of the flask containing a reactant under reduced pressure was repeated three times so that the system was thoroughly purged with nitrogen. In the flask were additionally placed 60 mL of toluene, 1.59 mL of trimethylsilyl trifluoromethanesulfonic acid, and 2.79 g of β-D-ribofuranose-1,2,3,5-tetraacetate, and the mixture solution thus prepared was heated under reflux for 2 hours at 80° C. After the solvent was then removed therefrom by using a rotary evaporator, the reactant was subjected to purification by silica gel chromatography (chloroform:methanol=95:5). Fractions containing the target substance were collected, and the eluent was then removed from the fractions to obtain 2.79 g of 2',3',5'-O-acetyl-2-N-acetyl-8-(4-ethylphenyl)azoguanosine (reference numeral 4 in the chem. 16).

In a two-necked eggplant-shaped flask, 2.79 g of 2',3',5'-O-acetyl-2-N-acetyl-8-(4-ethylphenyl)azoguanosine was placed, and nitrogen purging of the flask under reduced pressure was repeated three times so that the system was thoroughly purged with nitrogen. In the two-necked eggplant-shaped flask, 30 mL of methanol and 30 mL of ammonia (methanol solution) were additionally placed, and the mixture solution thus prepared was stirred for 6 hours at 60° C. After the reaction, a deposit was collected by filtration and then washed with methanol to obtain 1.57 g of 8-(4-ethylphenyl)azoguanosine (reference numeral 5 in the chem. 16).

(2-2) Synthesis of 5' Nucleoside (8EPA-Cap) with 5' Cap Structure Having Azo Skeleton containing the target substance were collected, and the solvent was then removed from the fractions to obtain 8-(4-ethylphenyl)azoguanosine monophosphate (reference numeral 2 in the chem. 17).

TABLE 5

$^1$H NMR (D$_2$O, 400 MHz) δ: 7.53 (d, J = 8.0, 2H), 7.21 (d, J = 8.0, 2H), 6.43 (d, J = 4.9, 1H), 5.17 (t, J = 5.4, 1H), 4.65 (t, J = 5.4, 1H), 4.29 (dd,

[Chem. 17]

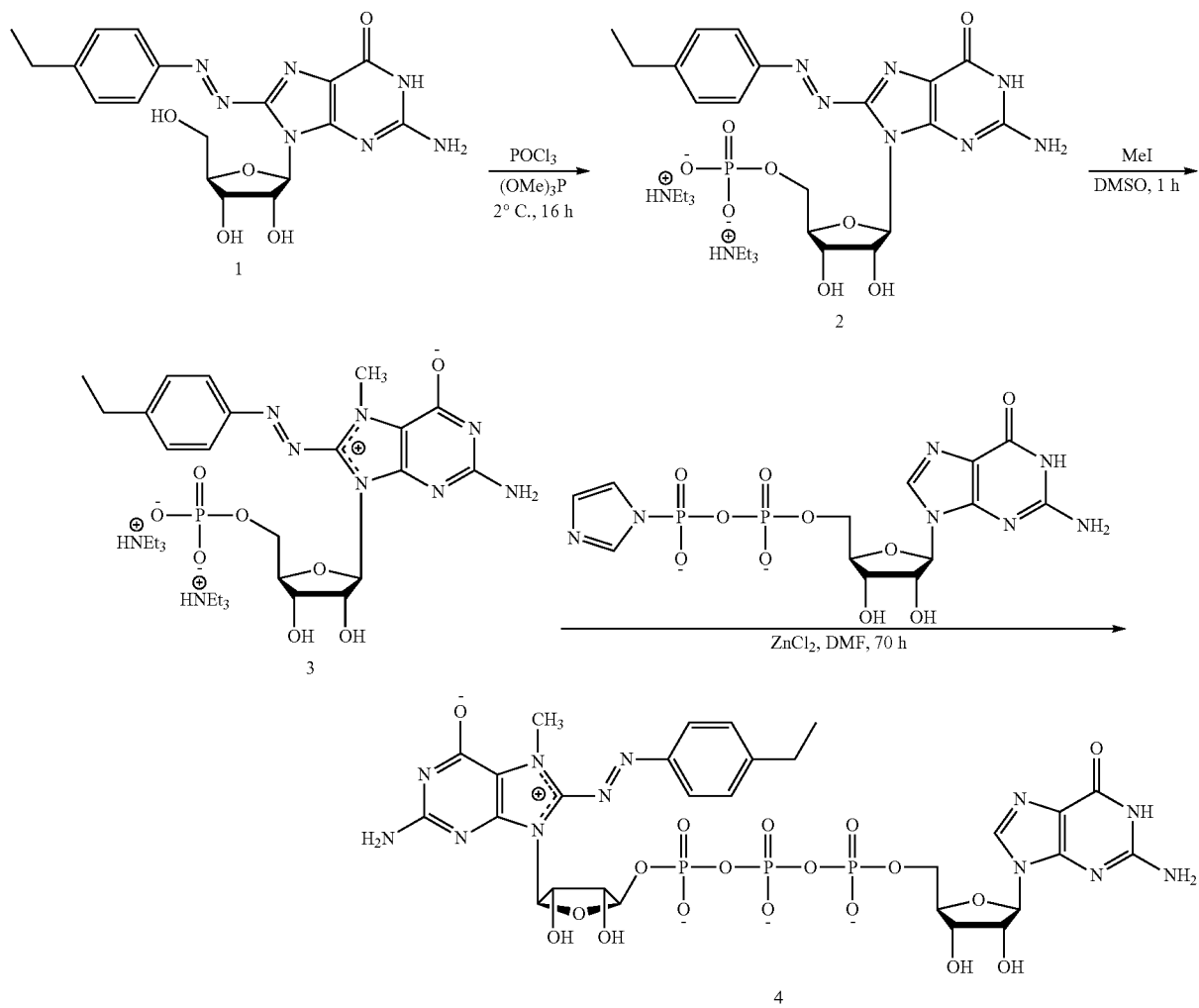

In a two-necked eggplant-shaped flask, 3 g of 8-(4-ethylphenyl)azoguanine (reference numeral 1 in the chem. 17) was placed, and nitrogen purging of the flask under reduced pressure was repeated three times so that the system was thoroughly purged with nitrogen. In the two-necked eggplant-shaped flask, 100 mL of trimethyl phosphate and 1.17 mL of phosphoryl chloride were additionally placed, and the mixture solution thus prepared was stirred for 20 hours at 4° C. Thereafter, 20 mL of water was further added to the resulting solution, and 1M TEAB buffer solution was then added to the resulting solution to adjust pH of the reaction solution to 5.5. The reaction solution was purified by using DEAE Sephadex (0M to 1M TAEB). Fractions TABLE 5-continued J = 10.8, 5.4, 1H), 4.22-4.17 (m, 1H), 4.07-4.01 (m, 1H), 2.67 (dd, J = 15.2, 7.3, 2H); $^{31}$P NMR (D$_2$O, 400 MHz) δ: −3.10 (t, J = 15.7, 1P); FAB MS (M − H)$^-$ for C$_{18}$H$_{22}$N$_7$O$_8$P$_7$ Calculated: 494.12; Found: 494.13

In a two-necked eggplant-shaped flask, 1.37 g of monophosphate thus obtained was placed, and nitrogen purging of the flask under reduced pressure was repeated three times so that the system was thoroughly purged with nitrogen. In the two-necked eggplant-shaped flask, 70 mL of DMSO and 4.74 mL of methyl iodide were additionally placed. The mixture solution thus prepared was stirred for 1 hour at room temperature. To the reaction solution was added 100 mL of cold water, and the mixture solution was washed with 300 mL of diethyl ether three times. By using 1M aqueous solution of sodium bicarbonate, pH of an aqueous layer of the resulting solution was adjusted to 5.5, and purification was carried out by using DEAE Sephadex (0M to 1M TAEB). Fractions containing the target substance were collected, and the solvent was then removed from the fractions, after which purification was further carried out by HPLC (0.1 M TEAB/acetonitrile). In this manner, 8-(4-ethylphenyl)guanosine monophosphate methylated at position 7 was obtained.

$^1$H NMR (DMSO-d$_6$, 400 MHz) δ: 7.84 (d, J=8.3, 2H), 7.47 (d, J=8.3, 2H), 7.24 (s, 2H), 6.37 (d, J=6.3, 1H), 7.43 (s, 2H), 5.10 (t, J=5.8, 1H), 4.33-4.31 (m, 1H), 4.18-4.12 (m, 1H), 4.06-4.02 (m, 1H), 3.95-3.89 (m, 1H), 2.72 (dd, J=15.1, 7.3, 2H), 2.11 (s, 3H), 1.24 (t, J=7.3, 3H); $^{31}$P NMR (DMSO-d$_6$, 400 MHz) δ: −6.74 (m, 1P); FAB MS (M-H)$^-$ for C$_{19}$H$_{24}$N$_7$O$_8$P, Calculated: 508.13. Found: 507.77.

In a two-necked eggplant-shaped flask, 193 mg of compound thus obtained (reference numeral 3 in the chem. 17) was placed, and nitrogen purging of the flask under reduced pressure was repeated three times so that the system was thoroughly purged with nitrogen. In the two-necked eggplant-shaped flask, 14 DMF and 258 mg of zinc chloride were additionally placed. The mixture solution thus prepared was stirred for 60 hours at room temperature. The reaction solution thus obtained was poured into an aqueous solution in which 1.24 g of EDTA was dissolved, and TEAB buffer solution was then added to the resulting solution to adjust pH of the reaction solution to 5.5. Thereafter, purification was carried out using DEAE Sephadex (0M to 1M TAEB). Fractions containing the target substance were collected, and the solvent was then removed from the fractions to obtain 8EPA-cap (TEA salt). The 8EPA-cap thus obtained was exchanged into free acids by using a weak anion exchange column (Strata-X-AW, SHIGMA Co.) to obtain 85 mg of 8EPA-cap (reference numeral 4 in the chem. 17) that is the target compound.

Figure 3:
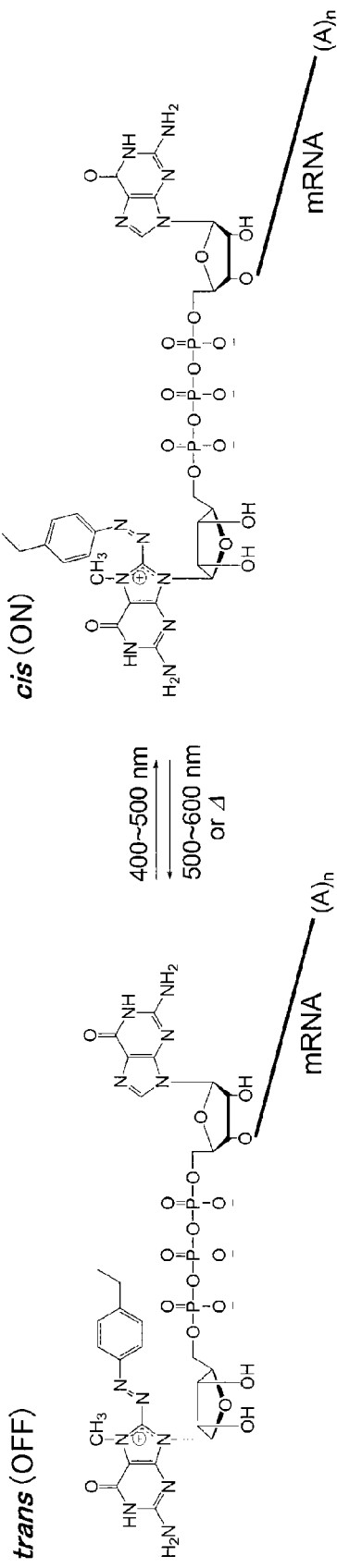
FIG. 3 is a view proving local regulation of intracellular translation of the GFP-coding RNA according to the present invention by fluorescence of the GFP.
Figure 3:
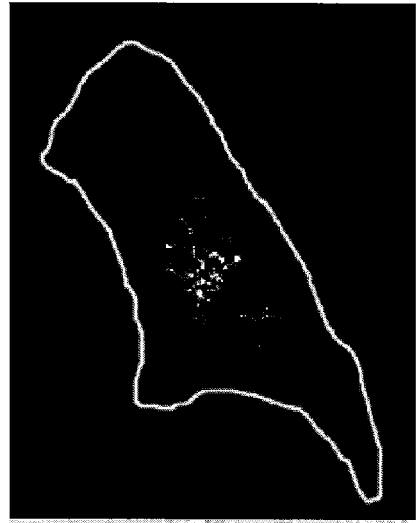
Figure 3:
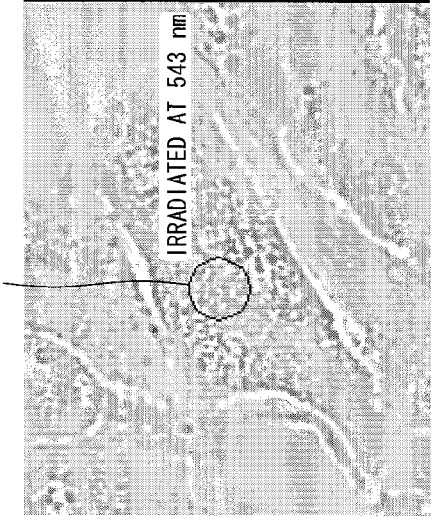

(2-3) Reversible Photoregulation of Intracellular Protein Translation of RNAs Containing Photoresponsive 5' Cap GFP-coding RNAs containing the photoresponsive 5' cap that had been synthesized in (2-2) were synthesized by using a cell-free transcription kit (MEGAscript, Ambion Co.). After the synthesis reaction, RNAs containing the 5' cap were purified by using an mRNA kit, MEGAclear (Ambion Co.). The RNAs obtained by using nuclease-free water were diluted to 2 μM and then injected into a HeLa cell by microinjection. After the injection, irradiation of a specific region in the cell with light of 458 nm and irradiation of the other region with light of 543 nm were carried out simultaneously for 30 minutes with a confocal laser scanning microscope. FIG. 3 shows the result of observation of fluorescence from GFP (lower part) and the structure of the RNA as used (upper part).

As shown in FIG. 3 (in the lower part), intense green fluorescence from the GFP was observed locally in a specific region that had been irradiated with light of 458 nm (in the lower part of FIG. 3; a left-hand region corresponding to a circled region in the picture on the left-hand side). That is, it was found that proteins were expressed only by the RNAs that had been changed into the cis form upon irradiation with light of 458 nm, while no proteins were expressed by the RNAs that had been changed into the trans form upon irradiation with light of 543 nm.

Note that the RNAs in the present Examples can be isomerized from the cis form to the trans form by the application of heat (e.g. room temperature), without irradiation with light of a wavelength ranging from 500 nm to 600 nm. In the upper part of FIG. 3, a symbol "Δ" in the wording "500 to 600 nm or Δ" denotes heat-induced isomerization of RNA (from the cis form to the trans form). That is, when a target region in the cell where translation is to be initiated is irradiated with, for example, light of 458 nm in a dark place, and the light irradiation is then suspended at room temperature, the RNAs in the present Examples can suppress the translation initiation and stop the subsequent protein expression. In the chems. 19 and 21, which will be described later, the symbol "Δ" also denotes the same.

Example 3

(3-1) Synthesis of Trans-8-Phenylazoguanosine

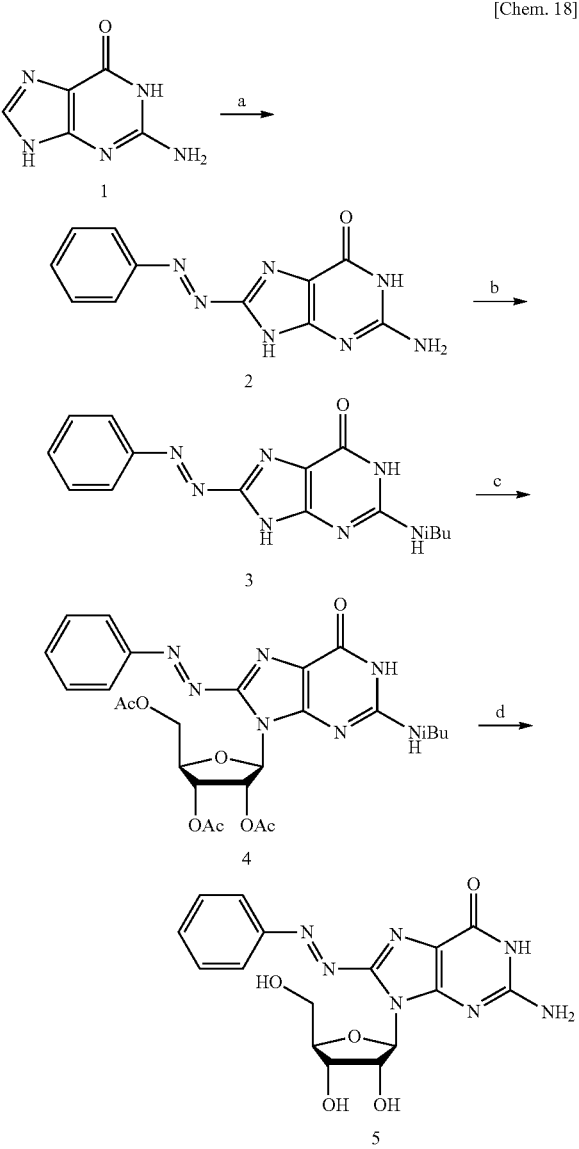

[Chem. 18]

Reaction a in the Chem. 18:

Solution A was prepared by adding 37% by weight of hydrochloric acid (6 ml) and aniline (549 ml) to 42 ml of water while cooling. Then, 1.5 g of guanosine was dissolved in 1.5% by weight of NaOH aqueous solution (300 mL), and the resulting solution was cooled in an ice bath. To the ice bath were added $NaNO_2$ (414 mg) aqueous solution and the solution A, and the mixture solution was stirred for 30 minutes at 0° C. After the reaction, a reactant was precipitated by addition of acetic acid, deposited, and allowed to stand for 2 hours. A deposit was collected by filtration to obtain 1.61 g of 8-phenylazoguanine (reference numeral 2 in the chem. 18).

Reaction b in the Chem. 18:

In a two-necked eggplant-shaped flask, 5.0 g of 8-phenylazoguanine was placed, and nitrogen purging of the flask under reduced pressure was repeated three times so that the system was thoroughly purged with nitrogen. In the two-necked eggplant-shaped flask, 75 ml of DMA and 8.2 ml of isobutyric anhydride were additionally placed, and the mixture solution thus prepared was heated under reflux for 1 hour at 150° C. After the reaction, a deposit was collected by filtration and washed with methanol to obtain 4.14 g of 2-N-isobutyl-8-phenylazoguanine (reference numeral 3 in the chem. 18).

Reaction c in the Chem. 18:

In a two-necked eggplant-shaped flask, 3.58 g of 2-N-isobutyl-8-phenylazoguanine was placed, and nitrogen purging of the flask under reduced pressure was repeated three times so that the system was thoroughly purged with nitrogen. In the two-necked eggplant-shaped flask, 100 ml of dichloroethane and 19.3 ml of N,O-bis(trimethylsilyl)acetamide were additionally placed, and the mixture solution thus prepared was heated under reflux for 1 hour at 80° C. After the reaction, the solvent was removed by using a rotary evaporator. Nitrogen purging of the flask containing a reactant under reduced pressure was repeated three times so that the system was thoroughly purged with nitrogen. In the flask, 100 mL of toluene, 2.39 ml of trimethylsilyl trifluoromethanesulfonic acid were additionally placed, 4.20 g of β-D-ribofuranose1,2,3,5-tetraacetate, and the mixture solution thus prepared was heated under reflux for 1.5 hours at 80° C. After the solvent was then removed therefrom by using a rotary evaporator, the reactant was subjected to purification by silica gel column chromatography (chloroform:methanol=95:5). Fractions containing the target substance were collected, and the eluent was then removed from the fractions to obtain 4.21 g of 2',3',5'-O-acetyl-2-N-isobutyl-8-phenylazoguanosine (reference numeral 4 in the chem. 18).

Reaction d in the Chem. 18:

In a two-necked eggplant-shaped flask, 1.14 g of 2',3',5'-O-acetyl-2-N-isobutyl-8-phenylazoguanosine was placed, and nitrogen purging of the flask under reduced pressure was repeated three times so that the system was thoroughly purged with nitrogen. In the two-necked eggplant-shaped flask, a 25 ml of methanol and 25 ml of methanol solution containing ammonia were additionally placed, and the mixture solution thus prepared was stirred for 4 hours at 60° C. After the reaction, a deposit was collected by filtration and washed with methanol to obtain 634 mg of trans-8-phenylazoguanosine (reference numeral 5 in the chem. 18).

(3-2) Reversible Photoisomerization Reaction of 8-Phenylazoguanosine

[Chem. 19]

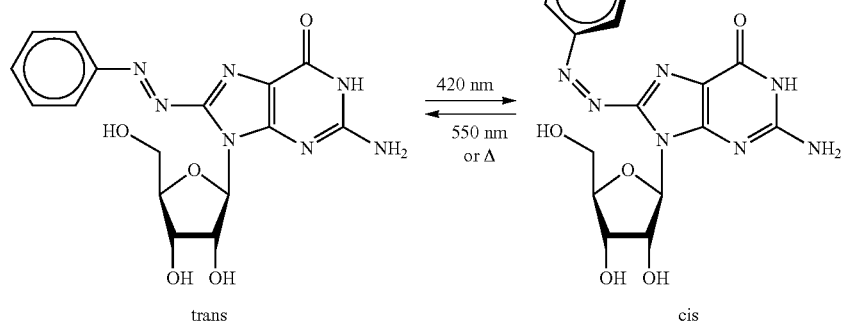

trans          cis (3-2-1) Photoisomerization Reaction from Trans Form (Trans-Isomer) to Cis Form (Cis-Isomer)

Figure 4:
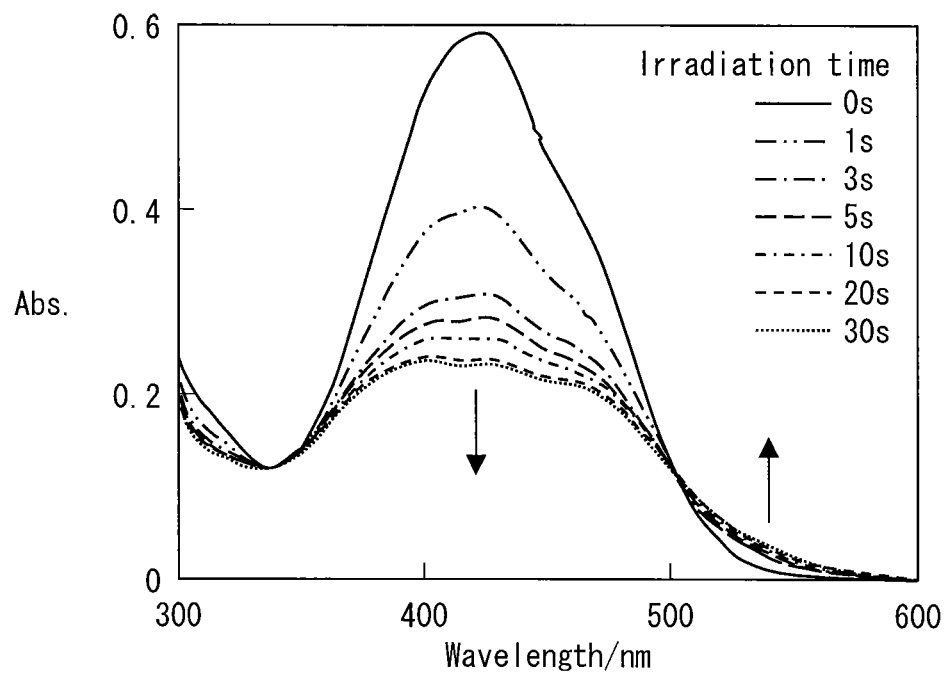
FIG. 4 is view showing time-dependent changes of absorption spectra of a compound obtained in Example 3 when irradiated with light at 420 nm (in a upper part) and light at 550 nm (in a lower part).
Figure 4:
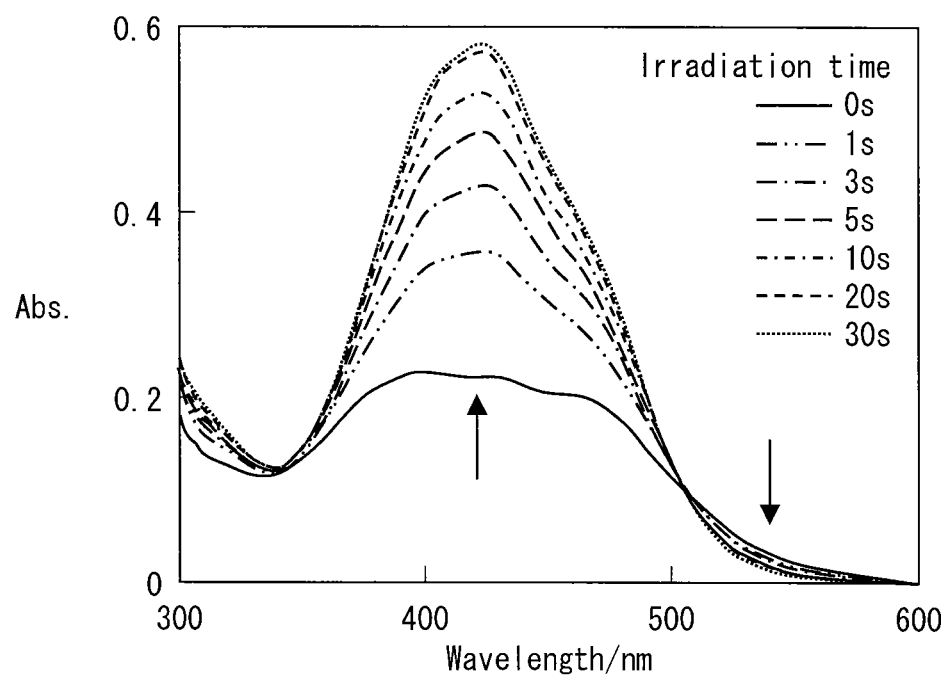

A stock solution was prepared by dissolving the 8-phenylazoguanosine obtained in (3-1) in methanol so that the 8-phenylazoguanosine presented at a concentration of 25 μM in the stock solution. In a quartz cell measuring 1 cm per side was placed 200 μl out of the stock solution thus prepared. The quartz cell was irradiated with visible light having a wavelength of 420 nm in a dark place, so that photoisomerization of the trans-8-phenylazoguanosine was assessed by measuring time-dependent changes of absorption spectra of the 8-phenylazoguanosine. In this assessment, MAX-301 manufactured by Asahi Spectra Co., Ltd. was used as a light source, and M.C.420/10 nm manufactured by the same manufacturer was used as a filter. The result is shown in FIG. 1. As shown in FIG. 4 (in the upper part), along with trans to cis photoisomerization of the trans-8-phenylazoguanosine, a peak of an absorbance at 420 nm decreased, and an absorbance at 500 to 600 nm increased. That is, it was found that the trans-8-phenylazoguanosine that had been in the trans form before irradiated with visible light was photoisomerized nearly completely to the cis form.

(3-2-2) Photoisomerization Reaction from Cis Form to Trans Form

Out of the stock solution prepared in (3-2-1), 200 μl of stock solution was isomerized to the cis form as described previously, after which the resulting product was placed in a quartz cell measuring 1 cm per side. The quartz cell was irradiated with visible light having a wavelength of 550 nm in a dark place, so that photoisomerization of cis-8-phenylazoguanosine was assessed by measuring time-dependent changes of absorption spectrum of the 8-phenylazoguanosine. In this assessment, MAX-301 manufactured by Asahi Spectra Co., Ltd. was used as a light source, and M.C.550/10 nm manufactured by the same manufacturer was used as a filter. The result is shown in FIG. 4 (in the lower part). As shown in FIG. 4 (in the lower part), along with trans photoisomerization of the cis-8-phenylazoguanosine, a peak of an absorbance at 420 nm increased, and an absorbance at 500 to 600 nm decreased. That is, it was found that cis-8-phenylazoguanosine that had been in the cis form before irradiated with visible light was photoisomerized nearly completely to the trans form.

(3-4) Alternate Cis-Trans Photoisomerization Reaction of 8-Phenylazoguanosine

Figure 5:
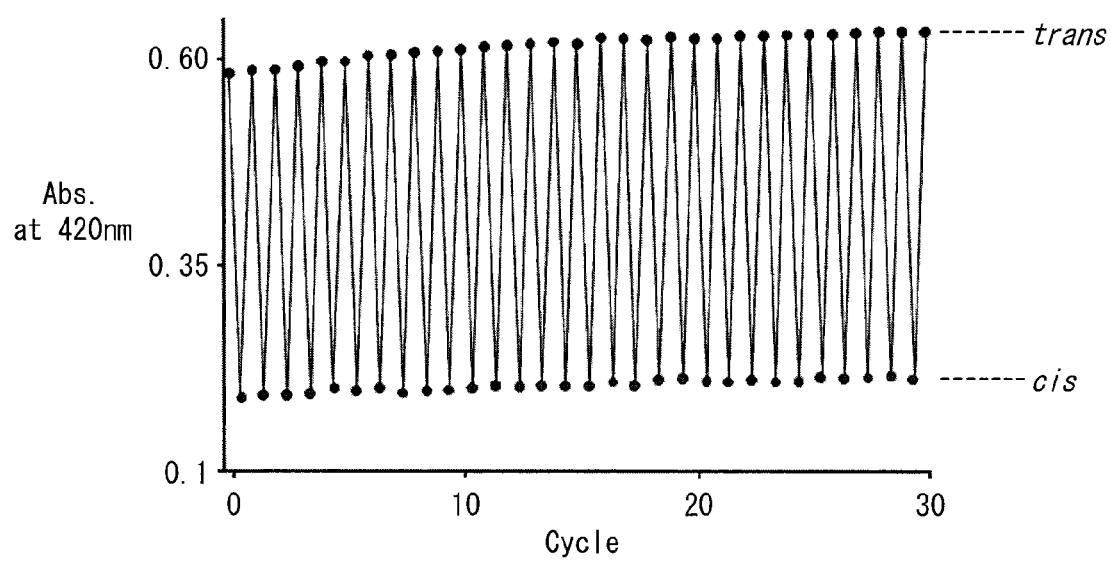
FIG. 5 is a view showing changes in absorbance of a compound obtained in Example 4 when alternately irradiated with light at 420 nm and light at 550 nm.

A stock solution was prepared by dissolving the trans-8-phenylazoguanosine obtained in (3-1) in methanol so that the trans-8-phenylazoguanosine presented at a concentration of 25 µM in the stock solution. In a quartz cell measuring 1 cm per side was placed 200 µl out of the stock solution. The quartz cell was alternately irradiated with visible light having wavelength of 420 nm and with visible light having a wavelength of 550 nm, each for 20 seconds, in a dark place. While this process was repeated in 30 cycles, an absorbance (420 nm) was measured. From the result of the measurement, durability of the compound against reversible photoisomerization was assessed. MAX-301 manufactured by Asahi Spectra Co., Ltd. was used as a light source, and M.C.420/10 nm and M.C.550/10 nm manufactured by the same manufacturer were used as filters. The result is shown in FIG. 5. As shown in FIG. 5, trans to cis and cis to trans photoisomerizations alternately took place in the 8-phenylazoguanosine in an appropriate manner. After 30 cycles of the alternate irradiations with light beams, no decomposition and side-reaction of the compound were found.

Example 4

(4-1) Synthesis of Trans-8-(p-Toluoylazo)Guanosine

[Chem. 20]

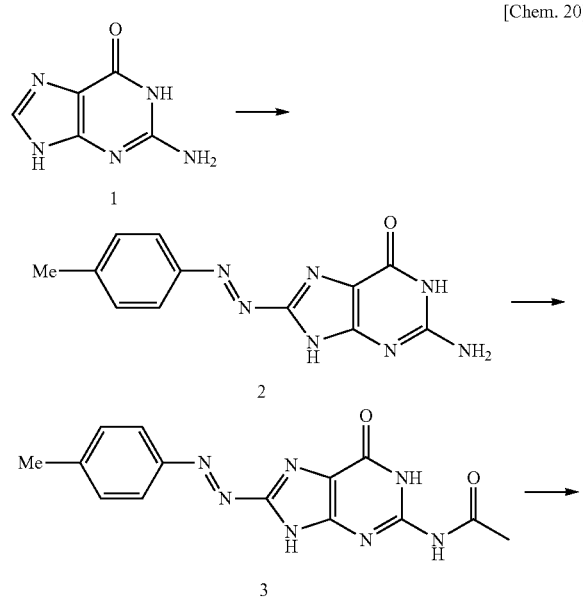

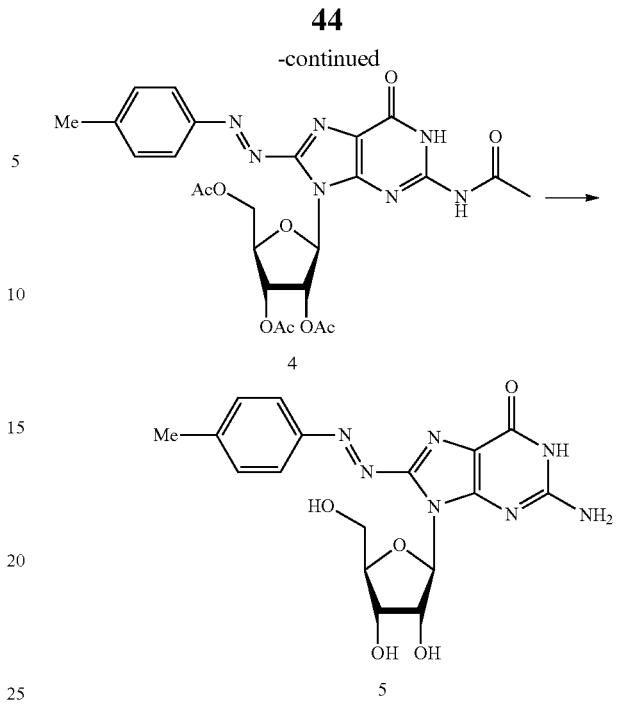

Reaction from 1 to 2 in the Chem. 20:

Solution B was prepared by adding 37% by weight of hydrochloric acid (4 ml) and 428 mg of p-toluidine to 28 ml of water. Then, 1.0 g of guanosine was dissolved in 1.5% by weight of NaOH aqueous solution (200 ml), and the resulting solution was cooled in an ice bath. To the ice bath were added NaNO$_2$ (275 mg) aqueous solution and the solution A, and the mixture solution was stirred for 30 minutes at 0° C. After the reaction, a reactant was precipitated by addition of acetic acid, deposited, and allowed to stand for 2 hours. A deposit was collected by filtration to obtain 1.17 g of 8-(p-toluoylazo)guanine (reference numeral 2 in the chem. 20).

Reaction from 2 to 3 in the Chem. 20:

In a two-necked eggplant-shaped flask, 1.0 g of 8-(p-toluoylazo)guanine was placed, and nitrogen purging of the flask under reduced pressure was repeated three times so that the system was thoroughly purged with nitrogen. In the two-necked eggplant-shaped flask, 15 ml of DMA and 0.7 ml of acetic anhydride were additionally placed, and the mixture solution thus prepared was heated under reflux for 3.5 hours at 160° C. After the reaction, a deposit was collected by filtration and washed with methanol to obtain 845 mg of 2-N-acetyl-8-(p-toluoylazo)guanine (reference numeral 3 in the chem. 20).

Reaction from 3 to 4 in the Chem. 20:

In a two-necked eggplant-shaped flask, 777 mg of 2-N-acetyl-8-(p-toluoylazo) was placed, and nitrogen purging of the flask under reduced pressure was repeated three times so that the system was thoroughly purged with nitrogen. In the two-necked eggplant-shaped flask, 30 ml of dichloroethane and 4.38 ml of N,O-bis(trimethylsilyl)acetamide were additionally placed, and the mixture solution thus prepared was heated under reflux for 1 hour at 80° C. After the reaction, the solvent was removed by using a rotary evaporator. Nitrogen purging of the flask containing a reactant under reduced pressure was repeated three times so that the system was thoroughly purged with nitrogen. In the flask were additionally placed 30 ml of toluene, 0.55 ml of trimethylsilyl trifluoromethanesulfonic acid, and 954 mg of β-D- ribofuranose-1,2,3,5-tetraacetate, and the mixture solution thus prepared was heated under reflux for 1.5 hours at 80° C. After the solvent was then removed therefrom by using a rotary evaporator, the reactant was subjected to purification by silica gel column chromatography (chloroform:methanol=95:5). Fractions containing the target substance were collected, and the eluent was then removed from the fractions to obtain 1.07 g of 2',3',5'-O-acetyl-2-N-acetyl-8-(p-toluoylazo)guanosine (reference numeral 4 in the chem. 20).

Reaction from 4 to 5 in the Chem. 20:

In a two-necked eggplant-shaped flask, 1.07 g of 2',3',5'-O-acetyl-2-N-acetyl-8-(p-toluoylazo)guanosine was placed, and nitrogen purging of the flask under reduced pressure was repeated three times so that the system was thoroughly purged with nitrogen. In the two-necked eggplant-shaped flask, 15 ml of methanol and 15 ml of methanol solution containing ammonia were additionally placed, and the mixture solution thus prepared was stirred for 4 hours at 60° C. After the reaction, a deposit was collected by filtration and washed with methanol to obtain 572 mg of cis-8-(p-toluoylazo)guanosine (reference numeral 5 in the chem. 20).

(4-2) Reversible Photoisomerization Reaction of 8-(p-toluoylazo)guanosine in the trans form before irradiated with visible light was photoisomerized nearly completely to the cis form.

(4-2-2) Photoisomerization Reaction from Cis Form to Trans Form

Out of the stock solution prepared in (4-2-1), 200 µl of stock solution was isomerized to the cis form as described previously, after which the resulting product was placed in a quartz cell measuring 1 cm per side. The quartz cell was irradiated with visible light having a wavelength of 550 nm in a dark place, so that photoisomerization of cis-8-(p-toluoylazo) guanosine was assessed by measuring time-dependent changes of absorption spectrum of the cis-8-(p-toluoylazo)guanosine. In this assessment, MAX-301 manufactured by Asahi Spectra Co., Ltd. was used as a light source, and M.C.550/10 nm manufactured by the same manufacturer was used as a filter. The result is shown in FIG. 6 (in the lower part). As shown in FIG. 6 (in the lower part), along with trans photoisomerization of the cis-8-(p-toluoylazo)guanosine, a peak of an absorbance at 420 nm increased, and an absorbance at 500 to 600 nm decreased. That is, it was found that the cis-8-(p-toluoylazo)guanosine

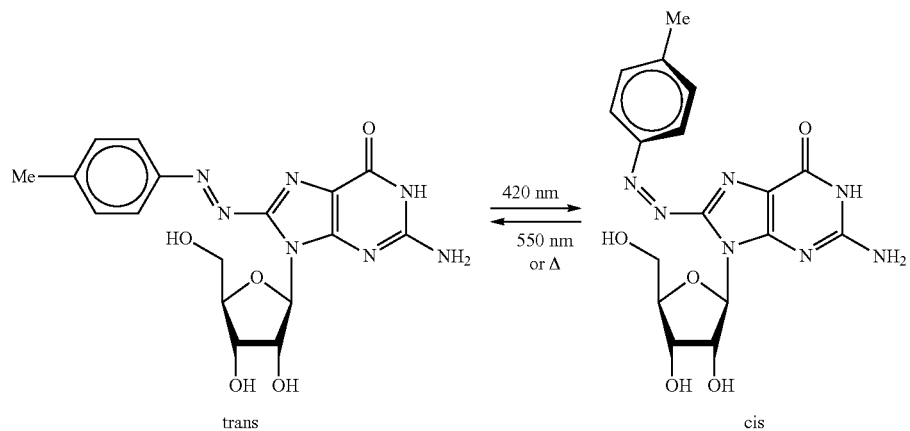

[Chem. 21]

(4-2-1) Photoisomerization Reaction from Trans Form to Cis Form

A stock solution was prepared by dissolving the trans-8-(p-toluoylazo)guanosine obtained in (4-1) in methanol so that the trans-8-(p-toluoylazo) guanosine presented at a concentration of 25 µM in the stock solution. In a quartz cell measuring 1 cm per side was placed 200 µl out of the stock solution thus prepared. The quartz cell was irradiated with visible light having a wavelength of 420 nm in a dark place, so that photoisomerization of the trans-8-(p-toluoylazo) guanosine was assessed by measuring time-dependent change of absorption spectra of the trans-8-(p-toluoylazo) guanosine. In this assessment, MAX-301 manufactured by Asahi Spectra Co., Ltd. was used as a light source, and M.C.420/10 nm manufactured by the same manufacturer was used as a filter. The result is shown in FIG. 6 (in the upper part). As shown in FIG. 6 (in the upper part), along with cis photoisomerization of the trans-8-(p-toluoylazo) guanosine, a peak of an absorbance at 420 nm decreased, and an absorbance at 500 to 600 nm increased. That is, it was found that the trans-8-(p-toluoylazo)guanosine that had been that had been in the cis form before irradiated with visible light was photoisomerized nearly completely to the trans form.

Example 5

(5-1) Synthesis of 8-phenylazo-2'-deoxyguanosine and introduction of 8-phenylazo-2'-deoxyguanosine into DNA

[Chem. 22]

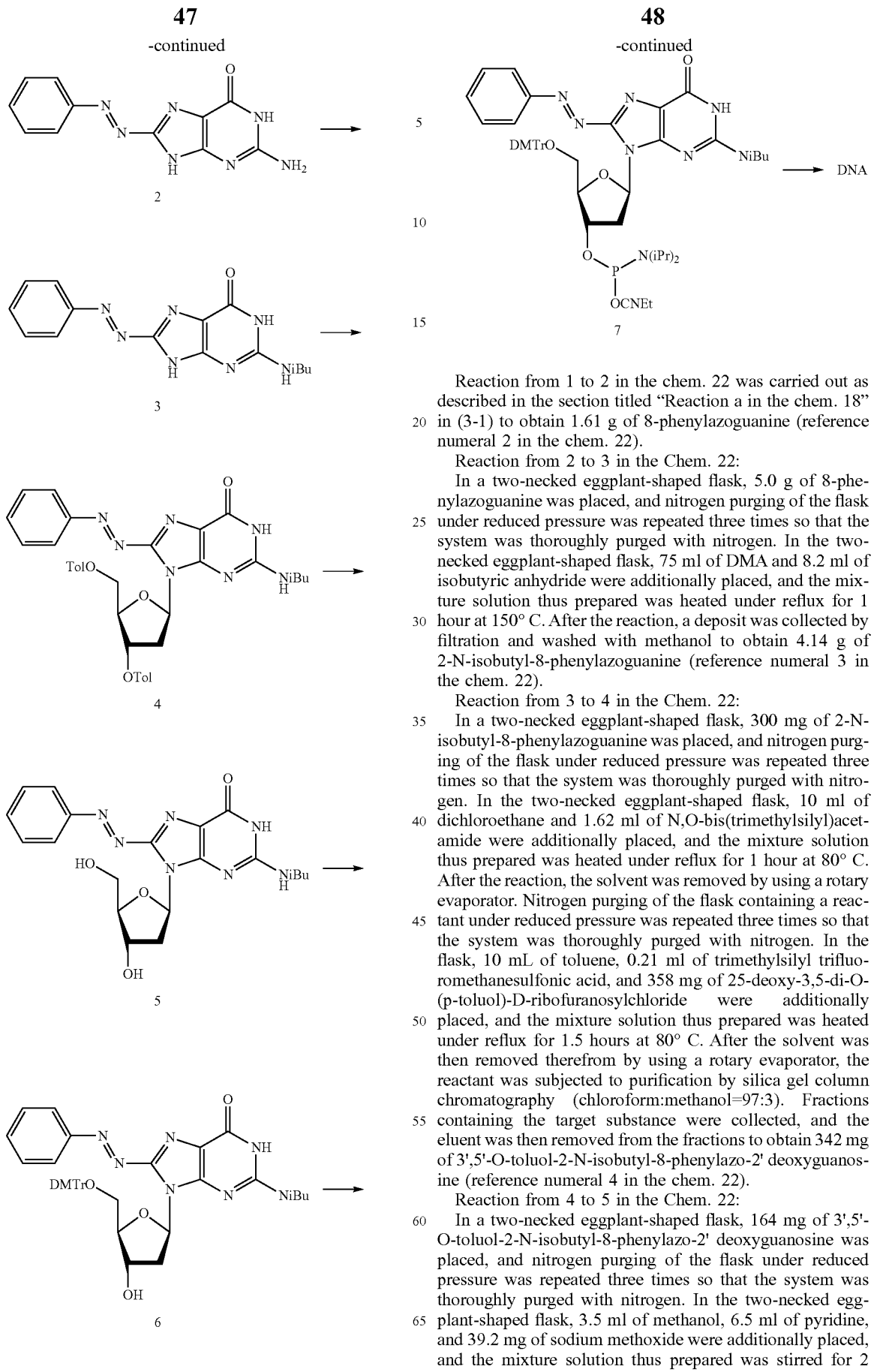

Reaction from 1 to 2 in the chem. 22 was carried out as described in the section titled "Reaction a in the chem. 18" in (3-1) to obtain 1.61 g of 8-phenylazoguanine (reference numeral 2 in the chem. 22).

Reaction from 2 to 3 in the Chem. 22:

In a two-necked eggplant-shaped flask, 5.0 g of 8-phenylazoguanine was placed, and nitrogen purging of the flask under reduced pressure was repeated three times so that the system was thoroughly purged with nitrogen. In the two-necked eggplant-shaped flask, 75 ml of DMA and 8.2 ml of isobutyric anhydride were additionally placed, and the mixture solution thus prepared was heated under reflux for 1 hour at 150° C. After the reaction, a deposit was collected by filtration and washed with methanol to obtain 4.14 g of 2-N-isobutyl-8-phenylazoguanine (reference numeral 3 in the chem. 22).

Reaction from 3 to 4 in the Chem. 22:

In a two-necked eggplant-shaped flask, 300 mg of 2-N-isobutyl-8-phenylazoguanine was placed, and nitrogen purging of the flask under reduced pressure was repeated three times so that the system was thoroughly purged with nitrogen. In the two-necked eggplant-shaped flask, 10 ml of dichloroethane and 1.62 ml of N,O-bis(trimethylsilyl)acetamide were additionally placed, and the mixture solution thus prepared was heated under reflux for 1 hour at 80° C. After the reaction, the solvent was removed by using a rotary evaporator. Nitrogen purging of the flask containing a reactant under reduced pressure was repeated three times so that the system was thoroughly purged with nitrogen. In the flask, 10 mL of toluene, 0.21 ml of trimethylsilyl trifluoromethanesulfonic acid, and 358 mg of 25-deoxy-3,5-di-O-(p-toluol)-D-ribofuranosylchloride were additionally placed, and the mixture solution thus prepared was heated under reflux for 1.5 hours at 80° C. After the solvent was then removed therefrom by using a rotary evaporator, the reactant was subjected to purification by silica gel column chromatography (chloroform:methanol=97:3). Fractions containing the target substance were collected, and the eluent was then removed from the fractions to obtain 342 mg of 3',5'-O-toluol-2-N-isobutyl-8-phenylazo-2' deoxyguanosine (reference numeral 4 in the chem. 22).

Reaction from 4 to 5 in the Chem. 22:

In a two-necked eggplant-shaped flask, 164 mg of 3',5'-O-toluol-2-N-isobutyl-8-phenylazo-2' deoxyguanosine was placed, and nitrogen purging of the flask under reduced pressure was repeated three times so that the system was thoroughly purged with nitrogen. In the two-necked eggplant-shaped flask, 3.5 ml of methanol, 6.5 ml of pyridine, and 39.2 mg of sodium methoxide were additionally placed, and the mixture solution thus prepared was stirred for 2 hours while cooling by using an ice bath. Thereafter, the resulting solution was stirred for 30 minutes at room temperature. After the reaction, a reaction solution was neutralized with 1M acetic acid, the solvent was removed by using a rotary evaporator, and purification was carried out by silica gel column chromatography (chloroform:methanol=95:5). Fractions containing the target substance were collected, and the eluent was then removed from the fractions to obtain 61 mg of 2-N-isobutyl-8-phenylazo-2' deoxyguanosine (reference numeral 5 in the chem. 22).

Reaction from 5 to 6 in the Chem. 22:

In a two-necked eggplant-shaped flask, 61 mg of 2-N-isobutyl-8-phenylazo-2'-deoxyguanosine was placed, and nitrogen purging of the flask under reduced pressure was repeated three times so that the system was thoroughly purged with nitrogen. In the two-necked eggplant-shaped flask, a pyridine solution prepared from 1.5 ml of pyridine, 3.4 mg of dimethylpyrimidine, and 4,4'-dimethoxytrityl chloride (46.8 mg) was additionally placed, and the mixture solution thus prepared was stirred for 2 hours at room temperature. After the solvent was then removed therefrom by using a rotary evaporator, the reactant was subjected to purification by silica gel column chromatography (chloroform:methanol=95:5). Fractions containing the target substance were collected, and the eluent was then removed from the fractions to obtain 44 mg of 5'-O-(4,4'-dimethoxytrityl)-2-N-isobutyl-8-phenylazo-2'-deoxyguanosine (reference numeral 6 in the chem. 22).

Reaction from 6 to 7 in the Chem. 22:

In a two-necked eggplant-shaped flask, 44 mg of 5'-O-(4,4'-dimethoxytrityl)-2-N-isobutyl-8-phenylazo-2'-deoxyguanosine was placed, and nitrogen purging of the flask under reduced pressure was repeated three times so that the system was thoroughly purged with nitrogen. In the two-necked eggplant-shaped flask, a pyridine solution prepared from 0.5 ml of pyridine, 1 ml of acetonitrile, and 0.021 ml of 2-cyanoethyl-N,N,N',N'-tetraisopropylphosphorodiamidite were additionally placed, and the mixture solution thus prepared was stirred for 1.5 hours at room temperature. After the solvent was then removed therefrom by using a rotary evaporator, the reactant was subjected to purification by silica gel column chromatography (chloroform:methanol=95:5). Fractions containing the target substance were collected, and the eluent was then removed from the fractions to obtain 37 mg of 5'-O-(4,4'-dimethoxytrityl)-3'-O-[2-cyanoethyl(N,N-diisopropylamino)phosphino]2-N-isobutyl-8-phenylazo-2'-deoxyguanosine (reference numeral 7 in the chem. 22).

Introduction of Photochromic Base into DNA:

5'-O-(4,4'-dimethoxytrityl)-3'-O-[2-cyanoethyl(N,N-diisopropylamino)phosphino]2-N-isobutyl-8-phenylazo-2'-deoxyguanosine was set in an automatic DNA synthesizer to synthesize an oligomer. The oligomer is represented by a sequence of 5'-TCAGTTXCGACA-3' (SEQ ID NO: 1), wherein an artificial base is introduced at X.

INDUSTRIAL APPLICABILITY

The present invention is expected to be applicable to biological and medical fields, particularly to a regenerative medical technology and the like technology.

The invention claimed is:

1. A method for regulating the amount of protein produced from an RNA containing a 5' cap structure and a coding region having an initiation codon at the 5' end of the coding region and a stop codon at the 3' end of the coding region, the RNA having a nucleoside compound introduced at a site selected from among the 5' cap structure and 10 bases from the 5' end of the RNA, wherein the nucleoside compound is such that a group is attached to (i) a carbon atom at position 8 of a purine nucleus or (ii) a carbon atom at position 5 or 6 of a pyrimidine nucleus, the group being represented by formula (I):

A-X=X-#                                        (I)

where A represents an aryl group or a heteroaryl group, # represents a site where the group represented by the formula (I) is attached to the carbon atom at the position 8 of the purine nucleus or the carbon atom at the position 5 or 6 of the pyrimidine nucleus, and two Xs, which are identical to or different from each other, each represents a nitrogen atom or CH whose H may be substituted by alkyl, comprising the step of:

irradiating the RNA with first light and/or with second light, the first light having a wavelength to change a structure of a nucleoside compound from a trans form to a cis form by irradiation of the first light, the second light having a wavelength, which is different from that of the first light, to change the structure of the nucleoside compound from the cis form to the trans form by irradiation of the second light, wherein the step of irradiating regulates translation of the RNA into protein, wherein the method is carried out in a cell free system or an in vitro eukaryotic cell.

2. The method according to claim 1, further comprising the step of:
   introducing the RNA into a cell,
   the step of irradiating is a step of irradiating, with the first light and/or the second light, the cell into which the RNA is introduced.

3. The method according to claim 1, wherein
   the first light and the second light are irradiated in this order or in reverse order in the step of irradiating.

4. The method according to claim 2, wherein
   the step of irradiating is a step of irradiating, with the first light, a spot where the RNA is introduced in the cell.

5. The method according to claim 4, wherein
   the step of irradiating is a step of simultaneously performing (i) the irradiation with the first light and (ii) irradiation of a region other than the spot with the second light.

6. The method according to claim 4, further comprising the step of:
   after the irradiation with the first light, irradiating a region including the spot with the second light.

7. The method according to claim 1, wherein
   the first light and/or the second light is visible light.

8. The method according to claim 4, wherein
   the spot measures approximately 1 μm to 5 μm in diameter.

\* \* \* \* \*

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Artificial oligonucletide
<220> FEATURE:
<221> NAME/KEY: misc_feature
<222> LOCATION: (7)..(7)
<223> OTHER INFORMATION: n is modified nucleotide

<400> SEQUENCE: 1
tcagttncga ca                                                         12
```